(12) United States Patent
Pfaff

(10) Patent No.: US 8,615,369 B2
(45) Date of Patent: Dec. 24, 2013

(54) METHOD OF IMPROVING THE RESOLUTION OF COMPOUNDS ELUTED FROM A CHROMATOGRAPHY DEVICE

(75) Inventor: Hans Pfaff, Bremen (DE)

(73) Assignee: Thermo Fisher Scientific (Bremen) GmbH, Bremen (DE)

( * ) Notice: Subject to any disclaimer, the term of this patent is extended or adjusted under 35 U.S.C. 154(b) by 407 days.

(21) Appl. No.: 12/868,408

(22) Filed: Aug. 25, 2010

(65) Prior Publication Data

US 2011/0054804 A1    Mar. 3, 2011

(30) Foreign Application Priority Data

Aug. 26, 2009   (EP) .................................... 09168748

(51) Int. Cl.
*G01N 30/04*   (2006.01)
*G01N 30/14*   (2006.01)
*G01N 30/10*   (2006.01)
*G01N 30/26*   (2006.01)

(52) U.S. Cl.
USPC .................... 702/25; 702/19; 702/23; 702/28

(58) Field of Classification Search
USPC ................. 702/19, 23, 25, 28, 179, 180, 183; 73/23.27; 250/341.6, 287
See application file for complete search history.

(56) References Cited

U.S. PATENT DOCUMENTS 5,473,162 A * 12/1995 Busch et al. ............... 250/341.6
6,865,926 B2 * 3/2005 O'Brien et al. ............. 73/23.27
7,057,168 B2 * 6/2006 Miller et al. ................. 250/287

FOREIGN PATENT DOCUMENTS

GB         2 404 194 A       1/2005
WO    WO 02/096540 A1      12/2002
WO    WO 2006/110848 A2    10/2006

OTHER PUBLICATIONS

Di Marco et al., "Mathematical Functions for the Representation of Chromatographic Peaks," J Chromatogr A. 2001, vol. 931 (1-2), pp. 1-30.
Sinha et al., "Algorithm for Locating Analytes of Interest Based on Mass Spectral Similarity in GC x GC-TOF-MS Data: Analysis of Metabolites in Human Infant Urine," J Chromatogr A. 2004, vol. 1058 (1-2), pp. 209-215.

(Continued)

*Primary Examiner* — Marc Armand
*Assistant Examiner* — Felix Suarez
(74) *Attorney, Agent, or Firm* — Charles B. Katz

(57) ABSTRACT

A method of and apparatus for improving the resolution of compounds eluted from a separation device are disclosed, particularly suited for use in the fields of gas or liquid chromatography. Embodiments of the invention provide that spectroscopic data are measured from an effluent eluted from a chromatography device as a function of elution time; peaks in intensity are identified to form a first set of identified peaks; peaks not due to an eluting compound are discarded from the first set of identified peaks thereby forming a second set of identified peaks from those retained; each peak in the second set of peaks is transformed into a first model peak centered on the elution time of each peak in the second set of peaks; some or all the model peaks created are added together to create a new chromatogram; and all identified peaks in intensity in the second set of peaks having elution times within a given time period of identified peaks in intensity in the new chromatogram are grouped together and assigned to a single eluted compound thereby forming a processed data set.

19 Claims, 7 Drawing Sheets

(56) References Cited

OTHER PUBLICATIONS

Hope et al., "Evaluation of the DotMap Algorithm for Locating Analytes of Interest Based on Mass Spectral Similarity in Data Collected Usindg Comprehensive Two-Dimensional Gas Chromatography Coupled with Time-Of-Flight Mass Spectrometry," J Chromatogr A. 2001, vol. 1086 (1-2), pp. 185-192.

Fredriksson et al., "An Objective Comparison of Pre-Processing Methods for Enhancement of Liquid Chromatography-Mass Spectrometry Data," J Chromatogr A. 2007, vol. 1172 (2), pp. 135-150.

Bruce N. Colby., "Spectral Deconvolution for Overlapping GC/MS Components," J Am Soc Mass Spectrom 1992, 3 (5), pp. 558-562.

S. E. Stein, "An Integrated Method for Spectrum Extraction and Compound Identification from Gas Chromatography/Mass Spectrometry Data," J Am Soc Mass Spectrom 1999, 10, pp. 770-781.

\* cited by examiner

METHOD OF IMPROVING THE RESOLUTION OF COMPOUNDS ELUTED FROM A CHROMATOGRAPHY DEVICE

CROSS-REFERENCE TO RELATED APPLICATIONS

This application claims the priority benefit of European Application No. 09168748.3, filed Aug. 26, 2009, entitled "Method of Improving the Resolution of Compounds Eluted from a Chromatography Device", which application is incorporated herein by reference in its entirety.

FIELD OF THE INVENTION

This invention relates to a method of improving the resolution of compounds eluted from a separation device. The method is preferably though not of necessity partially implemented in computer software, and may be utilised for analysis of liquid or gas chromatographic data.

BACKGROUND TO THE INVENTION

Chromatographic effluent, which may be liquid or gaseous in form, is routinely subjected to spectroscopic analysis, often mass spectrometry, in order to try and elucidate the eluting compounds contained in the effluent. For over three decades, computer control of mass spectrometer apparatus has enabled multiple mass spectra across a wide mass range to be acquired at a repetition rate that exceeds the elution period of any component of a complex mixture of a gas chromatographic effluent, for example, and this has allowed so-called mass chromatograms to be generated. Mass chromatograms are a record of the abundance of a mass measured from the effluent as a function of the elution or retention time, or scan number, as multiple mass spectral scans are performed during the elution period. Analysis of mass chromatograms enables the detection of eluted compounds which would otherwise be difficult or impossible to resolve, and can give information on the nature of the detected compounds.

Biller and Biemann (Anal. Lett., 7(7), 515-528, (1974)) described the analysis of mass chromatograms to produce so-called reconstructed mass spectra, which consist only of masses that have maximised in abundance at the same or closely matched elution times (the same or an immediately preceding scan number). This method produced simplified mass spectra at each scan number as all masses whose abundance was not maximising at or adjacent that scan number were rejected from the spectrum associated with that scan—increasing, steady and declining abundance mass signals were discarded from the spectrum leaving only those that maximise. This enabled less ambiguous identification of eluting compounds. As a further step, Biller and Biemann described combining all those masses which maximised in abundance at the same or closely matched elution times to create a so-called mass resolved gas chromatogram formed from the sum of the abundances of all such co-eluting mass peaks. The mass resolved gas chromatogram is similar in nature to the total ion chromatogram (TIC), but being composed only of masses whose abundance maximises at or close to the elution time, advantageously reveals previously hidden chromatographic structure, which allows eluting compounds to be more easily resolved graphically. However, in many situations, the resolution provided still may not be sufficient.

Dromey et. al. (Anal. Chem., 48(9), 1368-1375, (1976)) described accurately locating the elution time of components by analysis of mass chromatograms (fragmentograms, as termed by Dromey et. al.) which are only of masses unique to the eluting component relative to its neighbours—termed singlet peaks. The approach involved use of both the number of such singlets that maximise at a given elution time, and the total ion abundances above background at those maxima. They described their approach as looking for clusters of fragmentogram peaks. Analysis of the mass chromatograms included thresholding to remove background, in which a model peak profile was used, derived from the current data set. They extended their analysis to doublets and in theory to multiplets generally.

Colby (J. Am. Soc. Mass Spectrom., 3, 558-562, (1992)) described a so-called deconvoluted total ion current (DTIC) with a resolution of 0.1 scans using a three-point quadratic fit centroid calculation for peaks in the mass chromatograms, coupled with baseline correction (by an undisclosed method). Related masses were grouped on the basis of the retention time of the centroids, to a higher resolution than measurement interval.

Despite the advances provided by the prior art methods described above, there nevertheless remains a need to significantly improve the processing of chromatographic data, especially mass chromatographic data, e.g. to increase the ability to resolve and identify eluting compounds and/or reduce complexity of the processing. Against this background the present invention has been made.

SUMMARY OF INVENTION

According to an aspect of the present invention there is provided a method improving the resolution of compounds eluted from a chromatography device comprising the steps of:
(a) measuring spectroscopic data from an effluent eluted from a chromatography device as a function of elution time, the effluent containing eluted compounds;
(b) identifying at least some peaks in intensity as a function of time in at least some of the measured spectroscopic data to form a first set of identified peaks;
(c) discarding from the first set of identified peaks those peaks that are not due to an eluted compound thereby forming a second set of peaks from those retained;
(d) transforming each peak in the second set of peaks into a first model peak centred on the elution time of each peak in the second set of peaks;
(e) adding together some or all the model peaks created in step (d) to create a new chromatogram;
(f) identifying at least some peaks in intensity in the new chromatogram;
(g) grouping together all identified peaks in intensity in the second set of peaks having elution times within a given time period of identified peaks in intensity in the new chromatogram and assigning them to a single eluted compound thereby forming a processed data set.

According to another independent aspect of the present invention there is provided apparatus for improving the resolution of compounds eluted from a chromatography device, comprising:
(a) a device for measuring spectroscopic data from an effluent eluted from a chromatography device as a function of elution time, the effluent containing eluted compounds;
(b) a module for identifying at least some peaks in intensity as a function of time in at least some of the measured spectroscopic data to form a first set of identified peaks;

(c) a module for discarding from the first set of identified peaks those peaks that are not due to an eluted compound thereby forming a second set of peaks from those retained;
(d) a module for transforming each peak in the second set of peaks into a first model peak centred on the elution time of each peak in the second set of peaks;
(e) a module for adding together some or all the model peaks created in step (d) to create a new chromatogram;
(f) a module for identifying at least some peaks in intensity in the new chromatogram;
(g) a module for grouping together all identified peaks in intensity in the second set of peaks having elution times within a given time period of identified peaks in intensity in the new chromatogram and assigning them to a single eluted compound thereby forming a processed data set.

According to a further aspect of the present invention there is provided a method of identifying peptides eluted from a chromatography device comprising the steps of:
(a) measuring spectroscopic data from an effluent eluted from a chromatography device as a function of elution time, the effluent containing eluted compounds;
(b) identifying at least some peaks in intensity as a function of time in at least some of the measured spectroscopic data to form a first set of identified peaks;
(c) discarding from the first set of identified peaks those peaks that are not due to an eluted compound thereby forming a second set of peaks from those retained;
(d) transforming each peak in the second set of peaks into a first model peak centred on the elution time of each peak in the second set of peaks;
(e) adding together some or all the model peaks created in step (d) to create a new chromatogram;
(f) identifying at least some peaks in intensity in the new chromatogram;
(g) grouping together all identified peaks in intensity in the second set of peaks having elution times within a given time period of identified peaks in intensity in the new chromatogram and assigning them to a single eluted compound thereby forming a processed data set.

According to a still further aspect of the present invention there is provided a method of method of detecting differences between samples eluted from a chromatography device comprising the steps of, for each sample:
(a) measuring spectroscopic data from an effluent eluted from a chromatography device as a function of elution time, the effluent containing eluted compounds;
(b) identifying at least some peaks in intensity as a function of time in at least some of the measured spectroscopic data to form a first set of identified peaks;
(c) discarding from the first set of identified peaks those peaks that are not due to an eluted compound thereby forming a second set of peaks from those retained;
(d) transforming each peak in the second set of peaks into a first model peak centred on the elution time of each peak in the second set of peaks;
(e) adding together some or all the model peaks created in step (d) to create a new chromatogram;
(f) identifying at least some peaks in intensity in the new chromatogram;
(g) grouping together all identified peaks in intensity in the second set of peaks having elution times within a given time period of identified peaks in intensity in the new chromatogram and assigning them to a single eluted compound thereby forming a processed data set.
(h) comparing the grouped and assigned peaks from one sample with those from other samples.

According to a further method of the present invention there is provided a method of improving the resolution of compounds emitted from a separation device comprising:
(a) measuring spectroscopic data from an sample stream emitted from a separation device as a function of a separation dimension, the sample stream containing emitted compounds;
(b) identifying at least some peaks in intensity as a function of the separation dimension in at least some of the measured spectroscopic data to form a first set of identified peaks;
(c) discarding from the first set of identified peaks those peaks that are not due to an emitted compound thereby forming a second set of peaks from those retained;
(d) transforming each peak in the second set of peaks into a first model peak centred on the peak position in the separation dimension of each peak in the second set of peaks;
(e) adding together some or all the model peaks created in step (d) to create a new spectrum in the separation dimension;
(f) identifying at least some peaks in intensity in the new spectrum in the separation dimension;
(g) grouping together all identified peaks in intensity in the second set of peaks having peak positions in the separation dimension within a given distance in the separation dimension of identified peaks in intensity in the new spectrum in the separation dimension and assigning them to a single emitted compound thereby forming a processed data set.

The methods according to the present invention are suitable to be carried out using the apparatus according to the present invention.

The chromatography device may comprise a gas chromatograph, a liquid chromatograph or any other chromatographic system.

The measurement of spectroscopic data is an orthogonal spectroscopic measurement on the effluent from the chromatography device. The measured spectroscopic data generated from the eluted compounds may be, for example and without limitation hereto, mass spectra, optical spectra, ion mobility spectra, and NMR spectra. In a preferred embodiment the measured spectroscopic data generated from the eluted compounds are mass spectra. In relation to mass spectra, the invention functions with spectra that are measured in the mass or m/z domain but also functions with spectra that are measured in other domains, such as, e.g., frequency or time, where those domains are related to mass or m/z. Similarly, for optical spectra, ion mobility spectra etc. the invention may function with the spectra in any one of a number of different domains where such domains are related to each other (e.g. frequency or wavelength domains for optical spectra).

Herein, the term spectroscopic quantity is used to denote a portion of spectroscopic data.

The spectroscopic quantities measured from the eluted compounds are measured a plurality of times whilst the effluent from the chromatography device is eluted. The measured spectroscopic quantities from the eluted compounds are measured at least once during the period that a single compound is eluted from the chromatography device. Preferably the measured spectroscopic quantities from the eluted compounds are measured a plurality of times during the period that a single compound is eluted from the chromatography device.

The time at which the spectroscopic quantities from the eluted compounds are measured is also measured such that the spectroscopic quantities are measured as a function of the elution or retention time. (Retention time and elution time are terms used interchangeably herein.) For example, where the measured spectroscopic quantities are mass spectra, the intensity signal for a given m/z value in the spectra is measured as a function of time by measurement of the mass spectra a plurality of times. In practice, typically whole spectra (i.e. intensity signals for a range of m/z values) are measured as a function of time.

In both independent aspects of the present invention set out above, steps (b) to (g) may be performed with the aid of a computer, i.e. may be implemented in computer software. Alternatively steps (b) to (g) may be performed using specifically designed hardware to facilitate the processing of data, e.g. a dedicated electronic processor which does not use computer software. Preferably Steps (b) to (g) of the method of the present invention are performed with the aid of a computer running computer software. In general, any steps of the present invention which involve processing data are preferably implemented in computer software.

Step (b) of the method may comprise identifying some or all the peaks in intensity as a function of time in some or all of the measured spectroscopic data to form a first set of identified peaks. In some embodiments, all the peaks in intensity as a function of time in all of the measured spectroscopic data are identified. In other preferred embodiments, preliminary filtering of the measured spectroscopic data is undertaken prior to step (b) to reduce the time taken in the identification step (b), as will be further described, and consequently only some of the peaks in intensity as a function of time in some or all of the measured spectroscopic data are identified.

Identifying peaks in intensity may comprise identifying maxima in intensity (i.e. points of local maximum intensity), or alternatively or additionally identifying peak shapes (i.e. a series of sequential points having a rising and falling intensity profile). Identifying peaks in intensity may alternatively or additionally comprise identifying minima in intensity to infer a peak in intensity between the minima. Other means for identifying peaks in intensity may be conceived by those skilled in the art. In a preferred embodiment, identifying peaks in intensity comprises identifying maxima in intensity.

Preferably, prior to step (b), the method may comprise first identifying at least some peaks in intensity as a function of the spectroscopic data and second for at least some of said peaks collecting signal intensities from preceding and succeeding spectroscopic measurements within a spectroscopic window containing said peak. This extracts the spectroscopic quantity as a function of time from the measured spectroscopic data. Following these steps, step (b) is performed.

In step (c), peaks within the first set of identified peaks are analysed to identify those peaks that are not due to an eluted compound and then said identified peaks are discarded. All the remaining peaks form a second set of identified peaks, the second set being a subset of the first set of identified peaks. The peaks within the second set of identified peaks are candidates for being due to an eluted compound, Not all peaks within the second set of identified peaks may be due to eluted compounds as in some cases it is unclear whether a peak should be retained or discarded. Preferably where it is unclear whether a peak should be retained or discarded the peak is retained.

Various analytical methods can be used to distinguish between peaks which may be due to an eluted compound and those that are not. Methods include comparison of the peak height with the height of a local background and comparison of the peak shape with the shape of a second model peak. Preferably peaks are determined not to be due to an eluted compound and other peaks are determined to be candidates for being due to an eluted compound on the basis of the peak height with the height of a local background of the spectroscopic data. In another embodiment peaks are determined not to be due to an eluted compound and other peaks are determined to be candidates for being due to an eluted compound on the basis of a comparison of the peak shape with the shape of a second model peak. In still another embodiment, peaks are determined not to be due to an eluted compound and other peaks are determined to be candidates for being due to an eluted compound on the basis of both the peak height with the height of a local background of the spectroscopic data and on the basis of a comparison of the peak shape with the shape of a second model peak.

In another embodiment the decision whether peaks, especially those of low intensity, may be due to an eluted compound or not is based on predicting the intensity and the number of points above a detection threshold in the spectroscopic data on the basis of ion statistics.

In all embodiments peaks that are not due to an eluted compound are discarded from the first set of identified peaks and the peaks retained form a second set of identified peaks.

In embodiments in which peaks are determined not to be due to an eluted compound and other peaks are determined to be candidates for being due to an eluted compound on the basis of the peak height with the height of a local background of the spectroscopic data, the local background is a measure of the intensity of the measured spectroscopic quantity (e.g. ion abundance of a given m/z) close to the identified peak in time, but preferably not at any other local maxima. Preferably, the local background is a measure of the intensity of the measured spectroscopic quantity between the identified peak and one or more adjacent identified peaks. Preferably, the local background is a measure of the intensity of the measured spectroscopic quantity at a local minimum which is close to the identified peak and may be between the identified peak and one or more adjacent identified peaks. Accordingly, the determination of the intensity of the peak above the local background preferably utilises an expression containing the term Imaximum/Iminimum, where Imaximum=intensity of the maximum of the identified peak and Iminimum=the intensity of a minimum of the measured spectroscopic quantity local to the maximum of the identified peak in elution time.

More preferably, the local background is a measure of the intensity of the measured spectroscopic quantity at the minima adjacent to the identified peak maximum; one minimum being the immediately preceding minimum in elution time, the other being the immediately succeeding minimum in elution time, relative to the identified peak maximum. The intensity of one or other minima may be used alone, or some function of the intensities of the two minima, such as an average of the intensities may be used. Preferably the intensity of the smaller of the two minima is used. Preferably, the determination of the intensity of the peak above the local background utilises an expression containing the term Imaximum/(min(minimum1, minimum2), where Imaximum=intensity of the maximum of the identified peak; minimum1=the intensity of the minimum of the measured spectroscopic quantity that immediately preceded the maximum of the identified peak in elution time; minimum2=the intensity of the minimum of the measured spectroscopic quantity that immediately succeeded the maximum of the identified peak in elution time, and min(minimum1, minimum2) is the minimum of minimum1 and minimum2.

Preferably the determination of the intensity of the peak above the local background includes one or more factors representative of the noise of the measured spectroscopic quantity. Preferably, step (c) is accomplished using a function which incorporates both: factors relating to the minimum that immediately preceded and the minimum that immediately succeeded the peak maximum in elution or retention time, and, a factor relating to the noise in the measured spectroscopic data. More preferably the factor relating to the noise in the measured spectroscopic data will be representative of the noise in the signal at or close to the peak maximum, or over the identified peak. Preferably the step (c) includes the calculation of a peak factor (PF) which is a function of the intensity of the identified peak, and at least one of: a noise on one or more of the measured spectroscopic quantities in the vicinity of the identified peak, and, the intensity of one or more minima in the vicinity of the identified peak. Preferably, the determination of the intensity of the peak above the local background utilises an expression containing the term Imaximum/max[Noise, (min(minimum1, minimum2)], where Imaximum=intensity of the maximum of the identified peak; Noise=the intensity of the noise of one or more of the measured spectroscopic quantities; minimum1=the intensity of the minimum of the measured spectroscopic quantity that immediately preceded the maximum of the identified peak in elution time; minimum2=the intensity of the minimum of the measured spectroscopic quantity that immediately succeeded the maximum of the identified peak in elution time, and min(minimum1, minimum2) is the minimum of minimum1 and minimum2. The term max[Noise, (min(minimum1, minimum2)] is the maximum of Noise and min(minimum1, minimum2).

It will be appreciated that additional terms such as constants and multiplying factors may be applied to the above expressions and terms without departing from the scope of the present invention.

Other methods of background subtraction, optionally using additional information, including information from previously measured data, including blanks, can be used, e.g. the methods disclosed in U.S. Pat. No. 7,197,401 or 5,672,869. For time-of-flight mass spectrometers, other methods of peak identification are used, such as, for example, the methods disclosed in US patent application 2003/0218129. Most preferably noise and peak determination are performed using the methods described in U.S. Pat. No. 7,657,387, summarised at column 2 lines 18-41.

A preferred embodiment utilises a peak factor defined by:

$$PF = \frac{I_{maximum}}{\max(\text{Noise}, \min(\text{minimum1}, \text{minimum2}))} - C \quad \text{equation (1)}$$

where:
$I_{maximum}$=intensity of the maximum of the identified peak;
Noise=the intensity of the noise of one or more of the measured spectroscopic quantities;
minimum1=the intensity of the minimum of the measured spectroscopic quantity that immediately preceded the maximum of the identified peak in elution time;
minimum2=the intensity of the minimum of the measured spectroscopic quantity that immediately succeeded the maximum of the identified peak in elution time;
min(minimum1, minimum2) is the minimum of minimum1 and minimum2; and
C is a constant.

The denominator in equation (1) is the maximum of: the Noise and, the minimum of: minimum1 and minimum2. As such, if the Noise is larger than the minimum of minimum1 and minimum2, and the intensity of the measured peak maximum is equal to the Noise, PF=1−C. In a preferred embodiment, C=1.0 so that in the case just described, PF=0. However C may be any value.

Using the function of equation (1) with C=1.0, a peak factor set within the range 1 to 50 is used as a threshold to distinguish between peaks that may be due to background and peaks that are due to eluted species, preferably a range 1-10, more preferably the peak factor threshold is set within the range 2 to 4; more preferably still, the peak factor threshold is set to 3.0. If the peak factor is less than the threshold set, the identified peak is taken to be due to background rather than due to an eluted species.

Preferably, the Noise is calculated from the measured spectroscopic quantities at or near the elution time T of the peak under consideration. Where the measured spectroscopic quantities are derived from mass spectra, the Noise may be calculated from one or more mass spectra acquired at or near time T. A preferred method of calculating the Noise where the measured spectroscopic quantities are derived from mass spectra uses a single mass spectrum acquired at time T in the following way. The mean intensity of all points in the mass spectrum is calculated, Imean1. The standard deviation of the intensities of all points in the mass spectrum is calculated, SD1. A first noise threshold is calculated as Imean1+3·SD1. All spectral points below this first noise threshold are identified as a noise set. The mean intensity of all points in the noise set is calculated, Imean2. The standard deviation of the intensities of all points in the noise set is calculated, SD2. The Noise is then calculated as Imean2+3·SD2.

However, it will be appreciated that other methods of calculating the Noise may be used, including methods employing further iterative steps of the preceding described method, as well as other methods. For example, another preferred method of calculating the noise uses a time trace of a spectroscopic quantity (e.g. a certain mass). The mean intensity of all points in the time trace is calculated, Imean1. The standard deviation of the intensity of all points in the time trace is calculated, SD1. A first noise threshold is calculated as Imean1+3·SD1. All time trace points below this first noise threshold are identified as a noise set. The mean intensity of all points in the noise set is calculated, Imean2. The standard deviation of the intensity of all points in the noise set is calculated, SD2. The Noise is then calculated as Imean2+3·SD2.

In a further preferred case, noise information has already been identified prior to the current analysis and is retrieved together with the stored time/spectral data set. This is especially useful if the data are compressed, e.g. by discarding of data identified as noise, or other compression methods, such as compressions using wavelet or other integral transforms and discarding data in such transformed space. Accordingly, the method may beneficially be applied to compressed or sparse data.

In the present invention, each identified peak of the second set of identified peaks determined in step (c) to be candidate for being due to an eluted compound is transformed into a first model peak centred on the elution time of the identified peak. The first model peak shape used to form the set may be Gaussian, modified Gaussian, Lorentzian, bell-shaped, parabolic, triangular, or any other shape representative of the chromatographic peaks of eluted compounds. Such a peak shape can also be empirically determined from the data at hand, e.g. by analyzing the precision of the measurement as a distribution and determining its moments. A modified Gaussian peak shape may be a Gaussian peak with a tail on one or both sides. Preferably the first model peak shape is Gaussian.

Other convenient peak shapes that may be utilised to form the first model peak shape are parabolas and triangles.

The properties of Gaussian peak shapes and distributions and their sums are very well known and favourable for most types of data analysis. Thus only very restrictive requirements to the computing times or very distinct knowledge of the precision of the measurements would suggest use of other than Gaussian functions, but such use is within the scope of the invention.

Where the first model peak shape is Gaussian, the Gaussian model peak has a full width at half height $Z1$, centred on the elution time of the identified peak maximum. Preferably $Z1$ is a measure of the precision of the chromatographic, e.g. time measurement. $Z1$ may be determined by observation of the variation of the determined positions in the chromatographic dimension for peaks which are known to be related to one another such that they should appear in the same position. The width $Z1$ of the first model peak shape may be set from a predetermined or calculated parameter or more preferably is calculated from the measured spectroscopic data. Preferably the width $Z1$ of the first model peak shape is a function of the elution time, more preferably a linear function, whose width increases with increasing elution time. Preferably the width $Z1$ of the first model peak shape is determined from elution profiles of measured spectroscopic data generated from the eluted compounds as measured in step (a) and is therefore determined on the basis of the effluent from the chromatography device which is being analysed. Elution profiles are peaks of intensity of the measured spectroscopic data that are known to be due to eluted compounds. Preferably a plurality of elution profiles is used, spanning a range of elution times, and an analytical function is created to generate a width $Z1$ of the first model peak shape at any elution time within the range. Preferably the first model peak shape is a Gaussian peak shape, and has a full width at half height (FWHH) which is a linear function of the elution time at which the peak with which it is to be compared occurred and a function of the intensity of the peak.

Some or all the model peaks created in step (d) are then added together to create a new chromatogram (step (e)). Preferably all the model peaks created in step (d) are then added together to create a new chromatogram.

The new chromatogram is than analysed and peaks in intensity are identified (step (f)). The identification of peaks in intensity is accomplished in a similar manner to that described in relation to step (b).

Interpolation may be used to assign an accurate time position.

Peaks in intensity identified in step (c) are then clustered or grouped together on the basis of their elution time relative to the position of the peaks determined in step (f). This enables spectroscopic data to be grouped together and linked to individual eluting compounds, which may enable the eluting compounds to be identified. In the present invention all identified peaks determined to be candidates for being due to an eluting compound having elution times within a given time period of one another or preferably having elution times within a given time period of the position of the peak determined in step (f) are grouped together and assigned to a single eluting compound, leaving all other identified peaks determined to be due to an eluting compound unchanged, thereby forming a processed data set.

A peak within the second set of peaks may be found to be associated with more than one peak identified in step (f). It is then preferably included into all groups having elution times within a given time period of identified peaks in intensity in the new chromatogram and optionally flagged as a peak that is close to more than one eluted compound.

The processed data set is outputted or further processed by for example comparing the processed data set to a library of data sets, processing the data set to extract subsets of data, performing quantitation, etc. After any such further processing of the processed data set, a resultant further processed data set may be outputted.

In embodiments in which in step (c) peaks are determined to be candidates for being due to an eluted compound and are retained and other peaks are determined not to be due to an eluted compound and are discarded on the basis of a comparison of the peak shape with the shape of a second model peak, the second model peak shape may be Gaussian, modified Gaussian, Lorentzian, bell-shaped, parabolic, triangular, or any other shape representative of the chromatographic peaks of eluted compounds. Such a peak shape can also be empirically determined from the data at hand, e.g. as an average measured peak shape. A modified Gaussian peak shape may be a Gaussian peak with a tail on one or both sides. The second model peak shape may be generated from a base peak such as a parabolic peak shape then modified to better match measured chromatographic peak shapes of eluted compounds. Preferably the second model peak shape is Gaussian.

The width $Z2$ of the second model peak shape may be set from a predetermined or calculated parameter or more preferably is calculated from the measured spectroscopic data. Preferably the width $Z2$ of the second model peak shape is a function of the elution time, more preferably a linear function, whose width increases with increasing elution time. Preferably the width $Z2$ of the second model peak shape is determined from elution profiles of measured spectroscopic data generated from the eluted compounds as measured in step (a) and is therefore determined on the basis of the effluent from the chromatography device which is being analysed.

It is well known that chromatographic peak shapes are usually not Gaussian, and that peaks eluting at the same time frequently have different widths which depend on the properties of the Compound eluting. The inventors found that in the method of the present invention, peak position determinations in data of high quality and which have a high signal to noise ratio are usually not harmed by the use of a non-matching peakshape, but that on the other hand noisy data, where the invention is most needed, are more reliably identified and positioned using a simple function, especially a Gaussian. However the additional degree of freedom of using for example a peak width that is a variable individual to every peak (as is, for example, used in Stein, S. E., J. Am. Soc. Mass Spectrom., 1999, 10, 770-781) typically leads to a worse position determination than the simple Gaussian model where the width is only a function global to the complete chromatogram.

Elution profiles used to determine the peak width $Z2$ are chosen to be peaks of intensity of the measured spectroscopic data that are known to be due to eluted compounds. Preferably a plurality of elution profiles is used, spanning a range of elution times, and an analytical function is created to generate a width of the second model peak shape at any elution time within the range. Preferably the second model peak shape is a Gaussian peak shape, and has a full width at half height (FWHH) which is a linear function of the elution time at which the peak with which it is to be compared occurred.

In some embodiments, the match between the shape of the identified peak and the second model peak shape is preferably determined using a correlation factor (CF). Correlation factors are preferably determined between each of the identified peaks and the second model peak shape, the correlation factor being representative of the match between the shape of each identified peak and the second model peak shape. Preferably the correlation factor is a function of the intensities of the identified peaks and the second model peak shape at a plurality of points across the peaks. A class of such functions includes sample correlation coefficients. Accordingly, in a preferred embodiment, the match between the shape of the identified peak and the second model peak shape utilises an expression including a sample correlation coefficient.

Preferably, in these embodiments step (c) is accomplished using a function describing a correlation factor (CF) which is a sample correlation coefficient, of the form:

$$CF = \frac{n \cdot \sum_n (IM \cdot ID) - \sum_n IM \cdot \sum_n ID}{\sqrt{\left[n \cdot \sum_n (IM \cdot IM) - \left(\sum_n IM\right)^2\right] \cdot \left[n \cdot \sum_n (ID \cdot ID) - \left(\sum_n ID\right)^2\right]}} \quad \text{equation (2)}$$

where:
n=number of points across the identified peak and across the model peak shape;
IM=model peak shape intensities;
ID=measured intensities across the identified peak.

In this case, the number of points across the identified peak and the number of points across the second model peak shape are chosen to be the same (i.e. n) and the intensities IM and ID are derived respectively from the second model peak shape and the measured spectroscopic quantity at each of the points, n. Preferably n is chosen to be the number of measured data points across the identified peak, i.e. such that the measured intensities across the identified peak ID are measured data points, requiring no interpolation.

Using the function of equation (2), a correlation factor set within the range 0 and 0.9 is used as a threshold to distinguish between identified peaks that may be due to background and identified peaks that are candidates for being due to eluting species, preferably a correlation factor set within the range 0.6 and 0.8 is used, more preferably a correlation factor set within the range 0.65 and 0.75 is used, more preferably still the correlation factor threshold is set to 0.7. If the magnitude of the correlation factor is less than the threshold, the identified peak is taken to be due to background rather than due to an eluting species.

Even when a correlation factor is not used during further processing it is very useful and preferred to use such a procedure of matching the data to this second model peak to obtain an accurate position and height of a peak.

In some preferred embodiments, one or more additional steps of filtering are applied to the measured spectroscopic data in or before step (c) to further improve the ability of the method to distinguish between identified peaks due to background and identified peaks due to eluting species, or to reduce the processing time required to perform the method. As preferred examples, three additional filtering steps will be described: signal to noise (S/N) filtering, spike rejection, and signal smoothing.

Signal to noise filtering may be applied in or before step (c), preferably in or before step (b), such that if the signal to noise ratio of a measured spectroscopic quantity is less than a predetermined or calculated threshold, that spectroscopic quantity has no further processing performed upon it. For example, if the orthogonal spectroscopic measurement is mass spectrometry, any mass (or mass to charge ratio) signal as a function of time that does not have a S/N greater than the threshold is taken to be a mass species that is not present in the eluting material. Use of this S/N filter thereby speeds up subsequent processing steps, as no peaks will be sought for in spectroscopic quantities where they are deemed not present in the eluting material.

Spike rejection may be applied to the measured spectroscopic data between steps (a) and (b) to identify and remove artefacts. However preferably spike removal is performed in step (c). In a preferred embodiment, spike removal is performed in step (c) before signal smoothing is applied. If spike removal is not performed before signal smoothing is applied, a proportion of the peaks assigned to an eluting compound are false positives due to smoothed spikes. Spike removal is preferably performed before signal smoothing to remove spikes from the measured spectroscopic data to reduce the number of such false positives. Suitable spike removal algorithms are known to the person skilled in the art which could be utilised for this purpose.

Signal smoothing is preferably applied to the measured spectroscopic data after step (c) and after spike removal. There are many signal smoothing algorithms known in the art which could be utilised by the skilled person for this purpose. As already described, when signal smoothing is applied, spike removal is an essential step, as otherwise, spikes may be smoothed and become indistinguishable from eluted compound peaks. Signal smoothing also reduces the number of false positives. Signal smoothing reduces the error in the elution time calculated for each peak, which enables eluted compounds to be better resolved.

A preferred method in step (c) is to identify peaks to be discarded on the basis of a comparison between the measured number of consecutive data points above an intensity threshold and the number of points expected to be above that threshold within a certain time window. Where the observed number of data points is significantly lower than the number expected (e.g. half as many) the data points are discarded as noise, or if the observed number of consecutive data points above the threshold exceeds the number expected then the data points are rejected as being due to background. This preferred method for step (c) discards peaks from the first set of identified peaks on the basis of measured peak intensity and measured peak width compared with expected peak intensity and expected peak width.

Optionally, following step (c), a subset of all identified peaks thereby determined to be due to an eluting compound may be formed and outputted, and/or may be further processed. The method in that case further comprises a step of outputting data representative of the separated compounds. The outputted data may be in numerical form, table form, graphical form or other form. Typically the list would be saved in electronic form, e.g. to fulfil regulatory requirements on data retention.

As part of step (d), transforming each peak in the second set of peaks into a first model peak centred on the elution time of each peak in the second set of peaks, the spectroscopic data in the second set of peaks would be smoothed and the peak positions would be obtained using the second model peak.

A major advantage of the invention is the suitability of the results for further use. The grouped peaks obtained in step (g) of the method of the present invention can be used for improved qualitative results like identification, database search, determination of elemental compositions based on identified isotopic groups, identification of MS/MS fragments from multiplexed or non-isolated precursor ions, including in-source fragmentation, as well as for improvement of quantitative analysis, e.g. iTraq or SILAC methods, or detection of differences in metabolites or peptides ("expression") between samples collected under different conditions.

In the present invention, outputting may be performed in any conventional manner, e.g. in hard copy (e.g. paper), soft copy (e.g. VDU screen) or other form, and as any type of output, e.g. numerical form, table form, graphical or other form. It will be appreciated that any data sets or subsets, e.g. acquired, processed or generated, in the present invention may be stored, temporarily or permanently, using any conventional data storage medium and/or outputted.

The identified peaks determined to be due to an eluting compound having retention times within a given time period of one another are preferably combined into a single peak centred on a elution time which is a function of the elution times of the identified peaks. Preferably the said identified peaks are combined into a single peak by simply adding them together and the resultant single peak has a peak maximum, width and centroid according to the intensities of the identified peaks that formed it. The given time period is preferably a function related to the uncertainty of the measured spectroscopic quantities in the time domain. Preferably the given time period is X times the standard deviation of the uncertainty of the measured spectroscopic quantities in the time domain, where X is a value between 1 and 6. More preferably the given time period is 3 times the standard deviation of the uncertainty of the measured spectroscopic quantities in the time domain.

The uncertainty of the measured spectroscopic quantities in the time domain is preferably determined on the basis of the difference in the measured elution times of spectroscopic species which should have the same elution time. In the case where the measured spectroscopic quantities are mass spectra, the uncertainty of the measured spectroscopic quantities in the time domain is preferably a function of the difference in the measured elution times of isotopes of the same molecular species.

The apparatus according to the present invention comprises a device for measuring spectroscopic quantities from an effluent eluted from the chromatography device as a function of elution time, which is preferably a spectrometer, e.g. a mass spectrometer or an optical spectrometer (e.g. UV, visible, infrared, Raman etc.). Most preferably, i.e. for the most preferred embodiment measuring mass spectra, the device for measuring spectroscopic quantities is a mass spectrometer. The chromatography device is therefore most preferably interfaced to a mass spectrometer (e.g. LC/MS or GC/MS), i.e. such that at least some of the effluent from the chromatography device passes into the mass spectrometer for measurement of the spectroscopic quantities. The mass spectrometer may be any suitable type of mass spectrometer, e.g. quadrupole, ion trap, time-of flight (TOF), FT-ICR, Orbitrap™ or any other commercially available type of mass spectrometer. An additional detector, e.g. an optical detector such as a PDA can be connected to the same chromatographic device and events can be identified in the same way and combined with the mass spectrometric information. The device for measuring the spectroscopic quantities generates data representative of the measured spectroscopic quantities which is then processed in accordance with the invention. The generated data may be stored in any suitable data storage means for processing.

The module for identifying at least some peaks in intensity as a function of time in the measured spectroscopic data is a type of data processing module. The data processing module may comprise, for example, a dedicated electronic device or a programmed computer. Typically, the data processing module comprises a programmed computer. Similarly, the modules for discarding from the first set of identified peaks those peaks that are not due to an eluted compound thereby forming a second set of peaks from those retained; for transforming each peak in the second set of peaks into a first model peak centred on the elution time of each peak in the second set of peaks; for adding together some or all the model peaks created in step (d) to create a new chromatogram; for identifying at least some peaks in intensity in the new chromatogram; and for grouping together all identified peaks in intensity in the second set of peaks having elution times within a given time period of identified peaks in intensity in the new chromatogram and assigning them to a single eluted compound thereby forming a processed data set, are types of data processing module. The data processing module may comprise, for example, a dedicated electronic device or a programmed computer. Typically, the data processing module comprises a programmed computer. Typically, the same programmed computer is used as the data processing module for all modules. The same programmed computer may additionally be the same computer which controls the device for measuring the spectroscopic data (e.g. mass spectrometer).

For performing one or more additional steps, one or more additional modules for performing such steps may be provided. Preferably, however, such additional steps are performed using one or more of the same modules already described and more preferably, such additional steps are performed using the same programmed computer as already described.

The apparatus preferably further comprises an outputting device for outputting data representative of the separated compounds. The outputting device may comprise an electronic display device (e.g. VDU screen) or printer, the outputting device being under the control of a computer, which is typically the same programmed computer already described.

It will be appreciated that features described herein in relation to the method of the present invention apply equally to the apparatus of the present invention.

In a further aspect, the present invention provides a computer program having elements of program code which, when executed, carry out the methods previously described. In still another aspect, the present invention provides a computer readable medium carrying said program.

The present invention provides an improved means for enhancing chromatographic data by performing orthogonal spectroscopic measurements and processing resultant data. Thus, the invention may enable compounds to be separated or resolved in the chromatographic data which might not be separated or resolved by other methods. The invention is easily implemented, e.g. partially in computer software.

It is to be understood that many different separation methods exist, which may have one or more separation dimensions. Even though this description has hitherto taken the primary example of chromatographic separation and hence has largely used the word "time" to signify a chromatographic dimension the method of the present invention may be utilised with separation devices other than chromatographic devices and with devices which separate in dimensions other than time. For example the method of the invention may be as well be used for evaluation of ion mobility—mass spectrometry data, where the separation dimension than may be a drift time or an acceleration or retardation voltage, or there may be liquid chromatography—ion mobility—mass spectroscopy having two separation dimensions: elution time and ion mobility, and ion mass as a further spectral dimension.

Further the method could as well be used for interpretation of electrophoretic gel separation, possibly with a surface desorption ionisation methods such as SIMS, MALDI, DESI, LD, Laserspray, etc., giving one or more spatial coordinates as separation dimensions.

Similarly many types of chromatography apparatus have a photodetector, such as e.g. a photodiode array as the sole detector or together with a mass spectrometer, e.g. a Fourier transform mass spectrometer, thus creating a data set with elution time as the separation dimension and wavelength and frequency or mass as two separate spectrometric dimensions. The spectrometric dimensions could be evaluated separately or correlated.

It will be understood that the separation and spectrometric dimensions could as well be mapped to physico-chemical properties of the eluents like ion mobility coefficients, mass, photometric resonance, polarity, size, etc., depending on the detection method.

In more general terms steps (d) and (e) may be viewed as a convolution or "smoothing" of data with first model peak shape and step (b) of the invention may be viewed as a deconvolution of data with a second model peak shape, wherein preferably the width of the first model peak is less than the width of the second model peak. The transformed data set thus produced in step (e) has than a higher resolution in the separation dimension which can be used to cluster signals to events in a way that all signals which are within a certain radius are considered to belong to the same event. This radius may for example be the FWHM of the first model peak in the separation dimension and the FWHM of a mass spectrometer in the spectrometric dimension.

Preferably all signals that are indistinguishable in the separation dimension are grouped together as one event, and all signals which are distinguishable within the precision of the separation are assigned to different events.

A further advantage of the invention is that the data points may be irregularly spaced in the separation dimension as well as in the spectral dimension. One of the benefits of the method is that it does not require treatment of the data as a complete multidimensional matrix but is ideally suited for sparse or compressed data such as is created by many high-resolution mass spectrometers or for example by multi reaction monitoring.

DETAILED DESCRIPTION

The present invention will now be described in more detail with reference to the following examples which are for illustration only and are not intended to and do not limit the scope of the invention.

Figure 1:
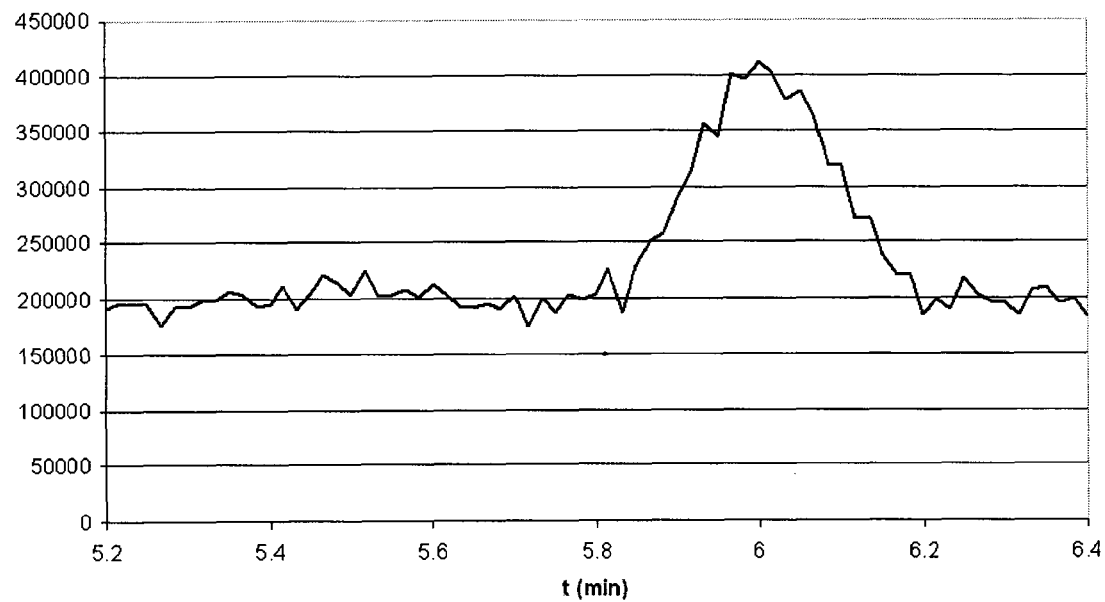
FIG. 1 shows a portion of a total ion chromatogram (TIC) elution profile such as would be produced from a liquid chromatograph, with ion intensity plotted against elution time.
Figure 2:
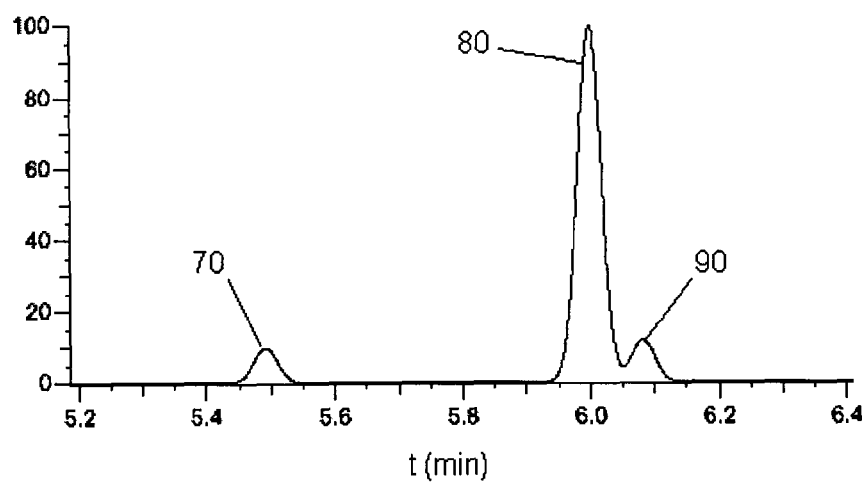
FIG. 2 shows a resolved TIC from the data of FIG. 1 using the present invention, with normalised intensity plotted against elution time.

An example of chromatographic data such as would be produced from a liquid chromatograph (LC) is shown in FIG. 1. The figure shows the total ion chromatograph (TIC) as would be measured by a mass spectrometer coupled to the eluted stream from the LC, i.e. the total current from all ionised species detected as a function of elution time (retention time). FIG. 1 shows the TIC for only a portion of the elution time, i.e. between 5.2 and 6.4 minutes. It can be seen that there is a single large peak, some smaller variations in intensity and a relatively large background. This is typical of a TIC measurement of the eluted stream from a LC. There are various compounds containing molecular species present within the eluted stream. Mass spectroscopic analysis is a method frequently used to determine which species are present, often involving MS/MS, in which molecules are fragmented in order to provide additional information on the species, to aid in the determination. It is not possible from FIG. 1 alone to determine the separate elution profiles of different species eluting from the chromatograph during the time span shown in FIG. 1. However, the present invention enables separate profiles to be determined with considerable detail. FIG. 2 shows the results of employing the method of the present invention.

From FIG. 1, it can be seen that the largest peak elutes over a time period of about 0.4 minutes, though this is difficult to determine with any accuracy, as the background is large and varies in time. The chromatogram of FIG. 2 shows peaks 80, 90 within the same time period along with a smaller peak 70 at an elution time ~5.5 minutes, and no apparent background. From visual inspection, the time resolution is better than 0.05 minutes, an improvement in resolution of a factor of 8.

This improvement in the present case is achieved by the use of mass-resolved data from the mass spectrometer using the method of the present invention. However, whilst the method will in the following example be described in relation to mass spectrometric data, the method of the present invention is not so limited. As has already been described, any additional spectroscopy technique that can be applied to chromatographic effluent stream and which is a so-called "orthogonal" technique to that of the chromatograph may be employed with the present invention.

As will have been apparent from the description above in relation to FIGS. 1 and 2, at least two important improvements are made to the chromatographic data by use of the method: removal of background, and enhanced time resolution. Both these enable the resolution of compounds eluted from a chromatography device to be improved.

Figure 3:
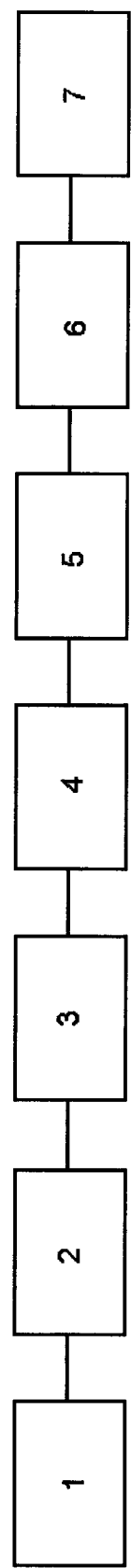
FIG. 3 shows a flow diagram illustrating the method of the present invention.

The method of the present invention is illustrated as a flow diagram in FIG. 3. The first step of the method, i.e. step (a) comprises measuring spectroscopic data generated from the eluted compounds as a function of elution time, Q(t), 1. In the following example, mass spectra are measured and mass chromatograms are formed from the mass spectral data, being the variation in intensity of a mass resolved quantity (ion abundance) as a function of the elution time. These mass chromatograms are in this example the measured spectroscopic data $Q(t)$.

Figure 4:
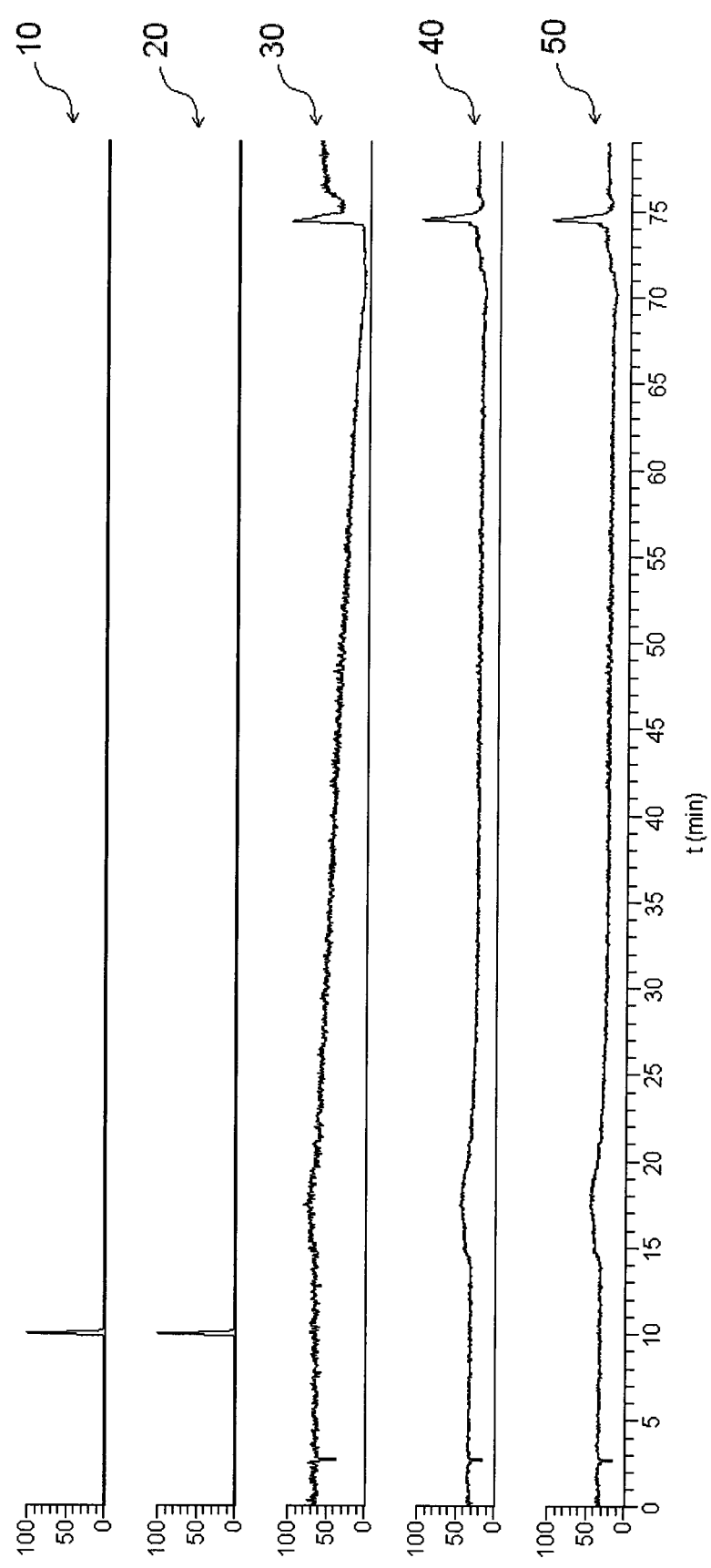
FIG. 4 shows five mass resolved measured spectroscopic quantities such as would be produced from the effluent from a liquid chromatograph with normalised intensity plotted against elution time.

The method further involves analysing the spectroscopic data to observe the variation of the various spectroscopically resolved quantities as a function of elution or retention time. Different mass peaks are analysed for their variation in elution or retention time, as compounds of the sample stream are eluted. As an example, FIG. 4 shows 5 mass resolved measured spectroscopic data, i.e. mass chromatograms, from the effluent, containing compounds from a LC, as a function of elution time. Mass chromatograms for nominal masses 271, 272, 167, 191 and 193 are shown at 10, 20, 30, 40 and 50 respectively. Mass chromatograms 10, 20 are of masses contained in eluting compounds but which are largely absent from the background, whilst 30, 40 and 50 are of masses present in the background. The data in FIG. 4 are from a different example to that used for FIGS. 1-2.

Having acquired the measured spectroscopic data $Q(t)$, the first stage of analysis, i.e. step (b) of the method, comprises identifying at least some peaks in intensity in at least some of the data $Q(t)$, 2 in FIG. 3 to form a first set of identified peaks. In a preferred embodiment, this step is accomplished using a computer. Maxima in intensity of the measured mass chromatograms are used to identify peaks. The computer typically identifies all maxima in intensity for each measured $Q(t)$, which in this example is the maximum in intensity of a mass (or more usually a mass to charge ratio as measured by a mass spectrometer) as a function of retention time. Herein, the term mass is used to refer to the measured spectroscopic data from a mass spectrometer. As will be appreciated, for many masses, the measured intensity of the mass is almost constantly changing with time, and consequently the number of maxima in intensity for each mass may be very large, as can be seen, for example, from the lower three plots of FIG. 4. Each of these lower three plots has some 600 maxima over the full chromatographic elution time period. For a mass resolution of 1 amu and a mass range of 200 to 2000 amu over a single, typical, chromatographic elution time, there may be of the order of a million maxima. With higher resolution mass spectrometers the number of maxima may be orders of magnitude higher. Hence the use of an automated analysis tool such as a computer is desirable.

The second stage of analysis then comprises determining whether the identified peaks are due to eluting compounds rather than anything else, such as the background. As will be appreciated, with millions of maxima per chromatographic run, it is to be expected that nearly all the peaks identified are not due to eluting compounds.

In step (c), peaks are discarded from the first set of identified peaks on the basis of the intensity of the peak maxima above the local background (e.g. a filter for the peak height), 3 in FIG. 3.

It is also possible to perform step (b) upon only a part of the data to be processed and then perform step (c) upon the processed results of step (b), remaining data being later processed in steps (b) and (c).

Figure 5:
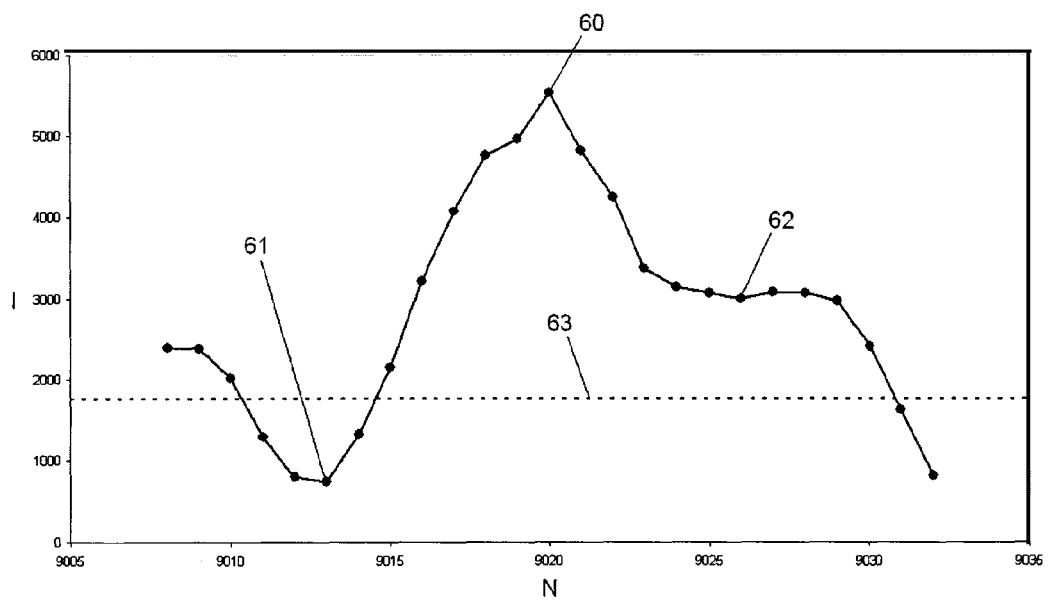
FIG. 5 shows a mass XYZ as a function of elution time, an identified maximum and two adjacent identified minima.

In applying the method step (c), for each peak, a measure of the local background is determined. The spectroscopic data $Q(t)$ is analysed in the vicinity of the identified peak maximum and two immediately adjacent minima are identified. FIG. 5 illustrates this process, showing a spectroscopic quantity, in this case mass 654.329 from a series of mass spectral scans, plotted as intensity, I, vs. scan number N. The figure shows identified peak maximum 60. One minimum is located at a retention time immediately preceding the identified peak maximum, 61, and one minimum is located at a retention time immediately succeeding the identified peak maximum, 62. One of these minima may be used as a measure of the local background. However, if the noise on the measurement of the spectroscopic quantity is significant, this is also taken into account. In FIG. 5 the noise level is shown as 63. In a preferred embodiment, the larger of: the noise on the measured spectroscopic quantity at the maximum, or the lowest intensity of the two identified minima, is used as a measure of the local background, according to equation (1). In the example shown in FIG. 5, minimum 61 is the lowest intensity of the two identified minima, but the intensity of minimum 61 is lower than the noise 63, and so the measure of the local background is in this case, the intensity of the noise, 63.

It will be noted that equation (1) defines peak factors in terms of the ratio of the intensity of the identified maximum and an intensity representative of the local background (be it due to noise, or one or more minima or other signals). Alternative formulations may be envisaged, such as:

$$PF = \frac{I_{maximum} - (\text{Noise}, \min(\text{minimum1}, \text{minimum2}))}{I_{maximum}} \quad \text{equation (3)}$$

Other formulations may be readily derived, including some that do not involve the use of a ratio of terms.

In use, the PF is typically limited to a maximum of 1000 to avoid excessively large numbers when the denominator approaches zero.

A preferred method of identifying peaks to discard in step (c) utilises a comparison between the number of measured data points above a threshold intensity and a number of points expected above that intensity. The number expected is calculated on the basis of the chromatographic peak width, the sampling rate and the signal to noise ratio of the measured data at the chromatographic peak apex. Where the number of measured data points on the peak in question is substantially fewer than the number expected, that peak is discarded as spurious. A spurious peak may for example have been due to a signal spike. Where the number of measured data points on the peak in question is substantially more than the number expected, that peak is discarded as being due to background. A preferred method of utilising this approach uses the second model peak. The second model peak shape is fitted to the measured peak in question, the intensity of the second model peak being matched to the intensity of the measured peak and the peak position of the second model peak being fitted to the peak position of the measured peak. The peak width of the second model peak is set to the peak width expected. From the sampling rate, the number of measured data points expected across the peak in question is known. By comparison with the second model peak, the expected intensity of each of these measured data points is predicted and is compared with the intensities actually measured. Where the measured data points have intensities that are larger than expected in comparison with the second mode peak the measured peak in question is discarded as being due to background. Where the measured data points across the peak in question have intensities that are smaller than expected in comparison with the second model peak the measured peak in question is discarded as being spurious. A preferred method uses an intensity threshold to compare the measured intensities to the intensities of the second model peak and only considers consecutive measured data points. For example, an intensity threshold set at 50% of the peak height may be used. Then, the number of consecutive measured data points in the peak in question that exceed the threshold is compared with the number expected based upon the width and position of the second model peak and the sampling rate of the data that was acquired. Where the number of consecutive measured data points in the peak in question above the threshold is too few, the peak is discarded is being spurious. Where the number of consecutive measured data points in the peak in question above the threshold is too many, the peak in question is discarded as being due to background. There will be a variation in the measured intensities of data points. The variation may be due to ion counting statistics and may follow a Poisson statistical distribution, for example. If the expected variation in measured intensities is known or may be estimated this may also be used to set the bounds for discarding peaks. When comparing the intensities of the consecutive measured data points with the threshold, the expected variation in intensity of each of those data points is calculated, (in the example of ion counting, the square root of the ion count expected is a measure of the variation in intensity to be expected). The intensity of the measured data points is then compared to the intensity expected, and measured data points are considered of unexpected intensity where they are above or below the expected intensity by more than the expected variation in intensity. Typically the variation in intensity expected increases for smaller signals, as is well known. Hence the criteria for rejecting peaks of smaller intensity will, by this method, be different from the criteria for rejecting peaks of larger intensity. The method of comparing the intensities of the measured data points across the expected peak width with the intensities expected may be supplemented by also examining the consecutive data points that extend beyond the expected peak width.

In step (d) of the method, each identified peak of the measured spectroscopic data in the second set of peaks that has been determined to be due to an eluting compound is transformed into a first model peak which comprises a Gaussian peak centred on the elution time of the identified peak, 4 in FIG. 3. The first model peak is, in this example, a Gaussian function which has: (i) the centre on the elution time of the identified peak, (ii) the height of the identified peak and (iii) the width as determined from the previously determined function of elution time and intensity. For convenience the first model peak will extend 3 to 6 times the width ("sigma") of the Gaussian function.

Some or all the Gaussian peaks are then added together to produce a new chromatogram, 5 in FIG. 3. The new chromatogram is shown in FIG. 2. Peaks are then identified in this new chromatogram, 6 in FIG. 3, in the same way as peaks were identified in step (b), described above, In step (g), identified peaks determined to be candidates to be due to eluted compounds are clustered on the basis of their elution time, 7 in FIG. 3. This enables spectroscopic data (masses, in this example) to be grouped together and linked to individual eluting compounds. This potentially enables the eluting compounds to be identified.

Ideally, all the mass chromatograms for the masses associated with the same eluting compound would peak at the same elution time. In practice, there will be measurement errors associated with the spectroscopic data, both in the measured intensity and in the measured time. Both will affect the measured elution time of a mass chromatographic peak. The elution time for a mass chromatographic peak is determined using one of three methods:

(i) a parabola is fitted to the three points of highest intensity and a maximum of the parabola is taken as the peak maximum, and the elution time derived;
(ii) a polynomial of degree m+1 is fitted to m data points around the measured peak apex, a maximum of the polynomial is taken as the peak maximum, and the elution time derived;
(iii) a modified Gaussian curve is fitted through the peak, a maximum of the Gaussian curve is taken as the peak maximum, and the elution time derived.

These are three preferred methods; others will be readily identified by those skilled in the art. The most preferred method is to fit the peak to the second model peak, this process yielding intensity and elution time.

The uncertainty of the measured spectroscopic data in the time domain is determined on the basis of the difference in the measured elution times of masses which should have the same elution time, and for this, molecular species having various isotopic components are used. The standard deviation of the variance in the elution time of the identified maxima from the various isotopic components is used to calculate a retention time error, which is a measure of the uncertainty of the measured spectroscopic data in the time domain. In a preferred method, the one hundred most intense peaks identified are used. It is assumed that these peaks represent the monoisotopic mass for the various species. The remaining identified peaks are then searched at masses with mass differences that are integer multiples of 1.0028 amu apart, plus or minus a mass tolerance, from the one hundred most intense peaks, in order to identify isotopic variants of those one hundred most intense peaks. Once isotopic variants have been determined, the difference in elution time between each isotopic variant and the relevant monoisotopic peak is calculated. The standard deviation of these time differences is then taken to be a measure of the uncertainty of the measured spectroscopic data in the time domain.

It has been found that this retention time error varies with the intensity of the maxima and the error is dependent on the acquisition conditions and the mass spectrometer and may be predicted for a given mass spectrometer using a function of the peak intensity. To take account of this, instead of basing the retention time error upon the standard deviation of all measured time differences, in a preferred method, the retention time error used is calculated according to the intensity of the peaks with which it is to be used, based on the standard deviation of time differences at different intensities. The retention time error as a function of intensity is calculated using a function of the form $A.\text{Intensity}^B$. This is determined by a fit to the measured data. Typical values for constants A and B are 0.8 and −0.35 respectively. Typically A is >0 and B<0.

This can be and preferably is combined with the retention-time dependency of the retention time uncertainty.

Having determined the elution time of each identified peak, and having calculated an expected uncertainty in the elution time measurements, identified peaks are clustered together into a single peak if their elution times fall within a time period that is less than or equal to plus or minus three times the uncertainty in the elution time measurements. It will be understood that other multiples of the uncertainty in the elution time measurements could be used if desired. In this way, mass chromatograms that peak at elution times within a given multiple of the uncertainty in the elution time measurements are taken to be masses that are from the same eluting compound.

The mass tolerance referred to above is a parameter that is a measure of the expected precision (reproducibility, not accuracy) of the mass values attributed within the mass spectra acquired during the chromatographic run. Accordingly it will depend upon the mass spectrometer used and the mass calibration of that spectrometer. For example, typically the Orbitrap™ mass spectrometer may have a mass tolerance of 5 ppm. The mass tolerance may be set by the user, or may be determined from the spectrometer.

Figure 6:
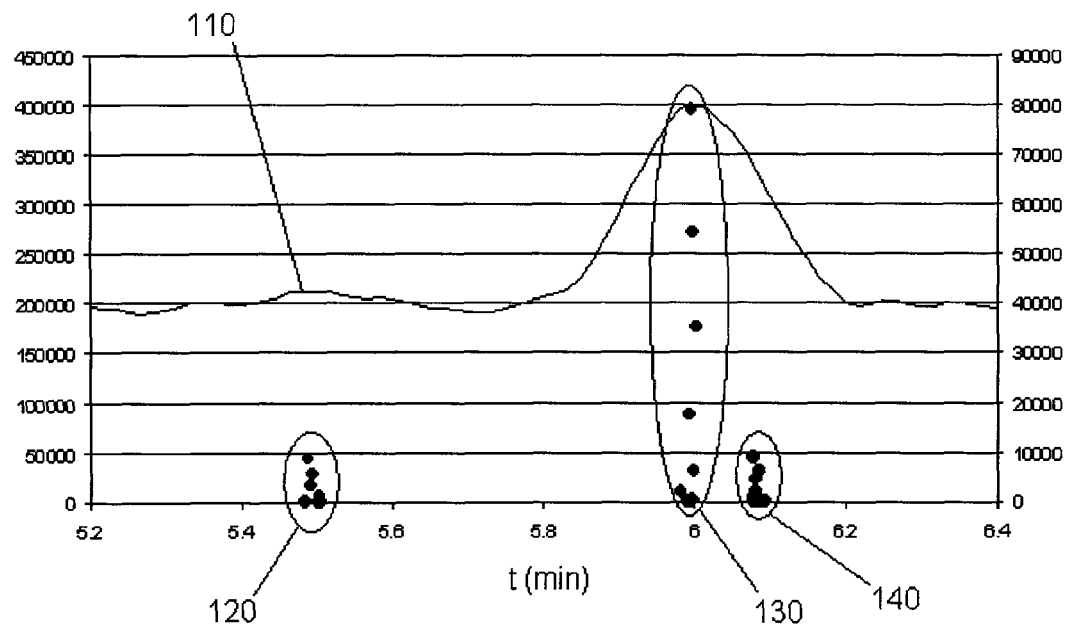
FIG. 6 shows a single smoothed TIC trace and three groups of points illustrating clustering, with intensity plotted against elution time.

A processed data set of identified peaks determined to be due to eluted compounds is created, in which those peaks that have elution times within a given time period of one another are combined into a single peak, leaving unchanged all other identified peaks. This processed data set then contains a list of resolved eluted compounds only, as identified by the method. FIG. 2 is an example of a portion of such a set, showing three resolved eluted compounds 70, 80, 90. FIG. 2 is illustrative of the advantages the method gives, when compared with FIGS. 1 and 6. FIG. 6 shows a single smoothed TIC trace 110 equivalent to the unsmoothed data of FIG. 1, in which it can be seen that only one well defined peak is visible. FIG. 6 also shows groups of points 120, 130, 140 in three clusters. These points denote the intensities and elution times of identified peaks that have been determined to be due to eluting compounds by the method of the present invention. The scale on the right of the figure gives the intensities of these identified peaks whilst the scale on the left of the figure gives the TIC trace intensity. The identified peaks have been converted to Gaussian peaks and then combined as described above, to form the trace shown in FIG. 2.

Optionally, in step (c), instead of distinguishing peaks on the basis of their height above a local background of the spectroscopic data, or as well as distinguishing peaks on the basis of their height above a local background of the spectroscopic data, a second filter selects identified peaks on the basis of the match between the shape of the identified peak and a model peak shape. The reference peak shape is a model peak, of Gaussian form. The full width at half height (FWHH) expected for an eluted compound varies with the elution time. In some embodiments the FWHH of the reference peak is set from a parameter, either predetermined or calculated at the time of use. In preferred embodiments the FWHH is set as a function of the elution time at which the identified peak with which it is to be compared was measured. Preferably the function is a linear function of the form:

$$FWHH(t) = a \cdot RT(t) + b \qquad \text{equation (4)}$$

where RT(t) is the retention time and a and b are coefficients. The coefficients a and b in equation (4) are derived from measured FWHH of peaks from the measured mass chromatograms at a range of retention times. Preferably the range spans the full elution time of the chromatographic run, or as much of it as possible. The widths of peaks from the measured spectroscopic data are determined as a function of the elution time and a least squares fit regression line is generated. In a second iteration only those peaks that have a width within one standard deviation of the regression line are retained, and from these peaks the coefficients a and b are calculated from a second regression line.

The reference peak shape can also be determined from one or more other data sets, retrieved from instrument information or entered by a user.

The reference peak shape is therefore a function of the elution time and accordingly a different reference peak shape is compared with each identified maximum where it occurred at a different elution time. The comparison is made using a correlation factor as defined in equation (2). A threshold correlation factor of 0.6 is used to filter identified maxima, with maxima having a correlation factor≥0.6 being taken to be due to eluted compounds.

The optional combination of peak height and peak shape filtering brings additional advantages. However further stages of filtering may bring additional benefits. As previously described, three additional stages of filtering are optionally applied. In a first stage, signal to noise filtering is applied, to eliminate spectroscopic quantities from further processing if the signal to noise ratio of the measured quantity is less than a threshold. As in this example where the spectroscopic quantities are masses, a threshold of 1.0 is typically applied, but a value between 1.0 and 50 may be used. This stage of filtering serves primarily to speed up the performance of the method as evaluation of the peak factor will also distinguish peaks that have too low a signal to noise ratio if the peak factor is evaluated as defined in equation (1), but eliminating spectroscopic quantities before evaluating the peak factor improves processing efficiency.

Spike rejection may also be applied. This stage of filtering also serves to speed up the performance of the method as evaluation of the correlation factor will also distinguish peaks that have a shape unlike a model peak, such as are due to a spike, if the correlation factor is evaluated as defined in equation (2). It may also serve to avoid false peaks being identified. This may occur when the data contains spikes and smoothing of the data is performed in such a way that the smoothed spike becomes similar in shape to the model peak. Spike rejection prior to smoothing is then essential. Spike rejection is accomplished by examination of adjacent points to each maximum. If the adjacent point preceding the maximum and the adjacent point succeeding the maximum are both zero in intensity within the measurement accuracy, i.e. less than the noise, the maximum is rejected as being a spike. More elaborate spike filters may use 5 or more points. Various spike removal algorithms will be known to those skilled the art, as for example used in audio processing, and it is also possible to perform spike-removal and smoothing in a single pass.

Signal smoothing is performed in preferred embodiments after spike rejection. Various signal smoothing algorithms will be known to those skilled in the art. A preferred form of signal smoothing is performed using the following method. An integer smoothing factor SM is calculated, where $$SM = (Scans_{total} * MOD_{FWHH} * 2)/(RT_{total} * 3)$$

where $Scans_{total}$ is the total number of scans in the data set from the chromatographic run, $MOD_{FWHH}$ is the full width half height of a model peak, $RT_{total}$ is the length of time of the chromatographic run. If SM is even, an integer 1 is added to make it odd. For simplicity this is described as if the measurement points where equidistant in time. But it is to be understood that all methods described here can easily be extended to non-equidistant data. The smoothed intensity of scan n, IntS[n], is then calculated from:

$$IntS[n] = \sum_{i=0}^{i=SM-1} Int[n - (SM-1)/2 + i] * Coeff[i]$$

where $$Coeff[i] = \frac{(SM - 2*(Abs((SM-1)/2 - i)))}{F}$$

-continued $$F = \sum_{i=0}^{i=SM-1} ((SM) - 2*\text{Abs}((SM-1)/2 - i)).$$

Figure 7:
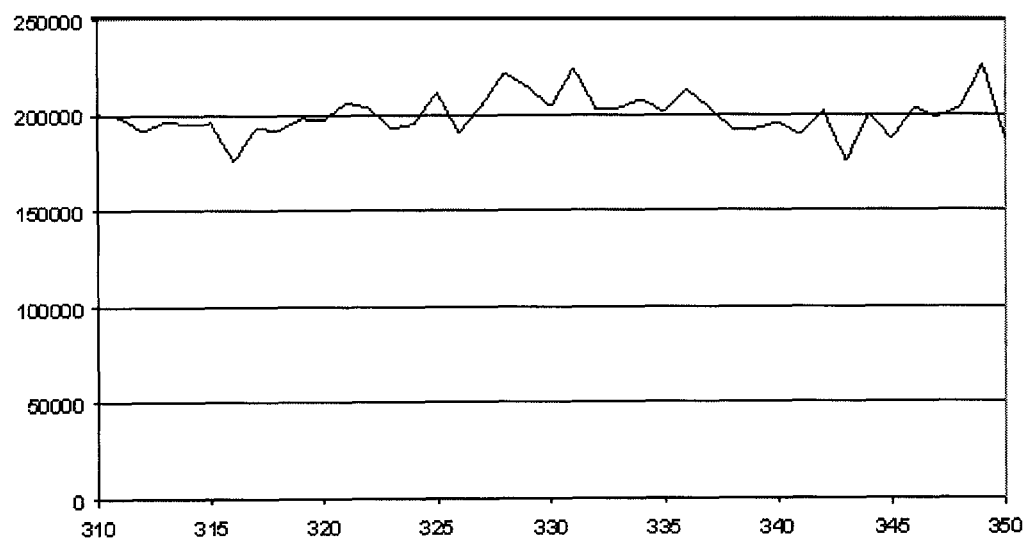
FIG. 7 shows a portion of the TIC of FIG. 1, with intensity plotted against scan number.
Figure 8A:
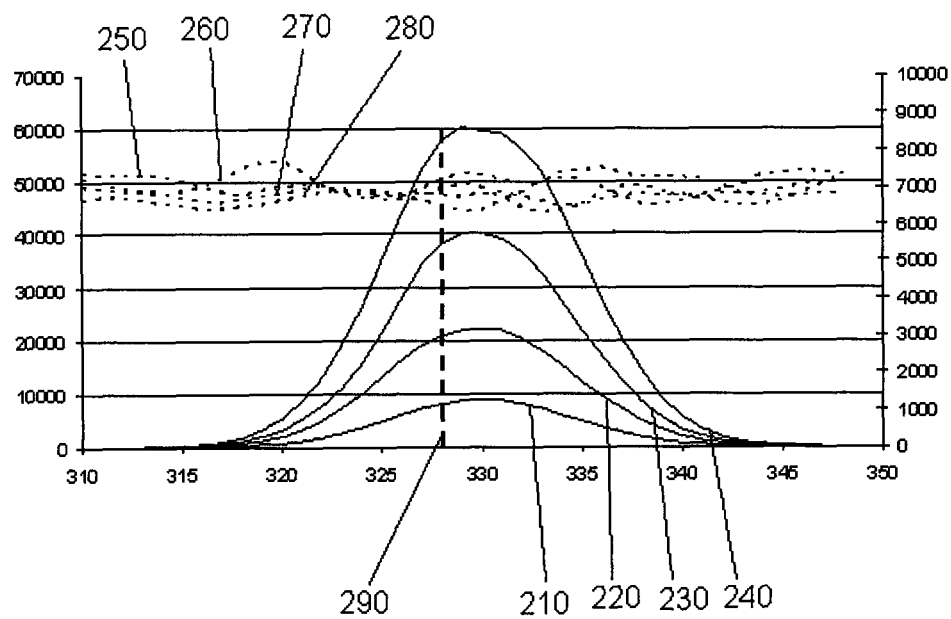
FIGS. 8a-8c show eight mass chromatograms and three different scan markers relating to the data of FIG. 7, with intensity plotted against scan number.

In one embodiment, the method from step (b) is performed in the following manner. A portion of the TIC of FIG. 1 is shown in FIG. 7, for the elution time 5.17 minutes to 5.83 minutes, plotted as intensity vs. scan number, where scan number is the mass spectral scan number performed on effluent from the chromatograph as a function of time. The portion of the total TIC plot shown in the figure, includes scans 310 to 350. In this embodiment the method from step (b) is performed by examining each mass spectral trace of a given scan and determining which masses have intensities greater than 1% of the intensity of the largest peak in the mass spectrum. All those masses are then examined as mass chromatograms in the vicinity of the scan number. An example of eight such mass chromatograms is given in FIG. 8. FIG. 8a shows the eight mass chromatograms for mass 832.6827 at 210, mass 831.6815 at 220, mass 830.6814 at 230, mass 829.6774 at 240, mass 381.7198 at 250, mass 635.5312 at 260, mass 508.6249 at 270, mass 254.8165 at 280 together with a vertical marker 290 at scan 328. In FIG. 8, traces 210, 220, 230, 240 are of lower intensity than traces 250, 260, 270 and 280. If all traces were plotted on the same scale, traces 210, 220, 230 and 240 would be difficult to discern, and so these traces have been re-scaled and the scale on the right side of the figure applies to them only, with the scale on the left side of the figure applying to traces 250, 260, 270 and 280.

Figure 8B:
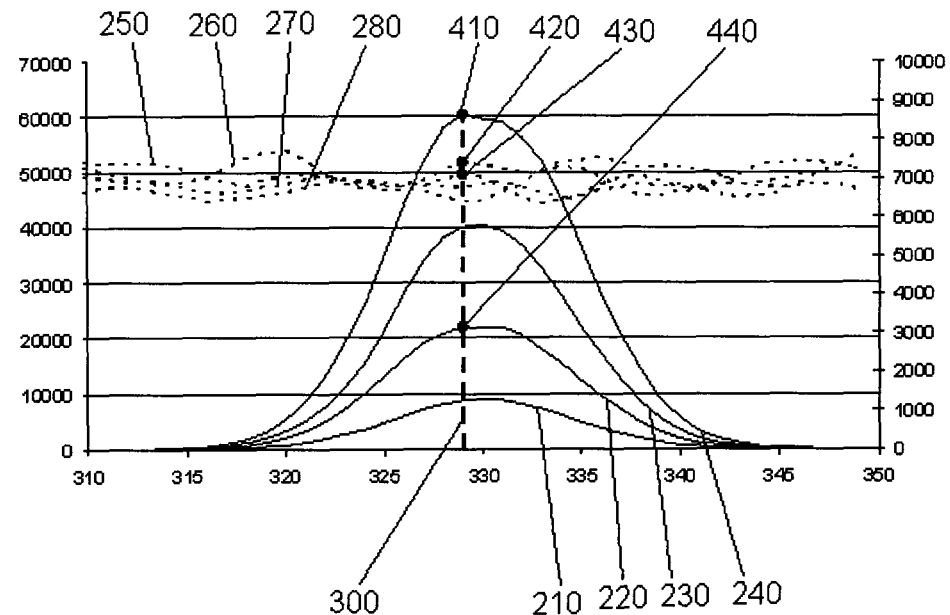

The mass chromatograms are then examined to determine if any of them have reached a maximum in intensity at the current scan number and if they have, then the peaks are identified as in step (b) of the method. Identified peaks are recorded in a results table, containing the mass and the elution time (calculated by one of the centroid methods previously described). In addition, at this stage step (c) is also performed upon the identified peaks, and peak factors and, in this example, correlation factors are calculated and also stored in the results table, together with a flag to denote whether the peak has been determined to be due to an eluted compound on the basis of the values of the peak factor and the correlation factor. The scan number is then incremented and the process repeated. It can be seen from FIG. 8a that no mass chromatogram 210-280 has a maximum in intensity at the elution time corresponding to scan 328. Consequently no entries are made to the results table. However FIG. 8b shows a similar plot with a marker 300 at scan 329. The mass traces 210-280 in FIG. 8b denote the same mass chromatograms as depicted in FIG. 8a. It can be seen from FIG. 8b that four of the mass chromatograms have maximum in intensity at an elution time corresponding to scan 329, and these are shown at 410, 420, 430, 440. Consequently four entries are made to the results table as shown in Table 1.

TABLE 1

Results table for scan 329.

| Mass | Peak Flag | Centroid Elution Time | Peak Factor | Correlation Factor |
|---|---|---|---|---|
| 254.8165 | Reject | 5.5004 | 0.08 | 0.6956 |
| 381.7198 | Reject | 5.4749 | 0.12 | 0.8672 |
| 829.6774 | Accept | 5.4996 | 1000 | 0.9644 |
| 831.6815 | Accept | 5.4965 | 1000 | 0.9751 |

As described earlier, in use, the PF is limited to a maximum of 1000 to avoid excessively large numbers when the denominator approaches zero and this has produced the values of exactly 1000 in the table.

Figure 8C:
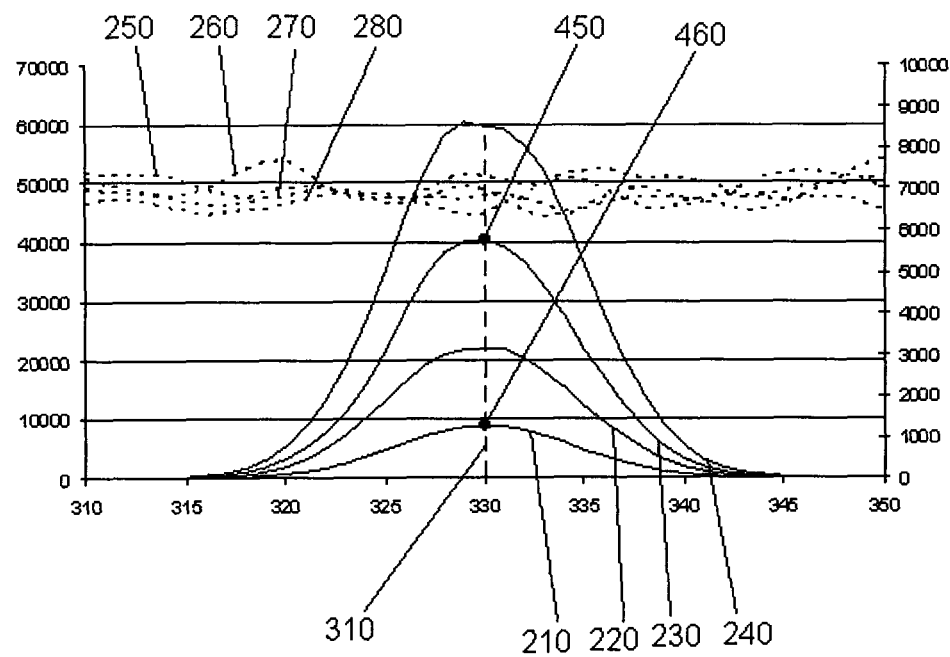

FIG. 8c shows the same eight mass chromatograms as in FIGS. 8a and 8b, together with marker 310 at scan 330. Two mass chromatograms have maximum in intensity at an elution time corresponding to scan 330, and these are shown at 450 and 460. Consequently two entries are made to the results table as shown in Table 2.

TABLE 2

Results table for scan 330.

| Mass | Peak Flag | Centroid Elution Time | Peak Factor | Correlation Factor |
|---|---|---|---|---|
| 830.6814 | Accept | 5.498 | 1000 | 0.9987 |
| 832.6827 | Accept | 5.4999 | 1000 | 0.9994 |

Once all scans have been examined in this manner, a list of peaks determined to be candidates for being due to eluted compounds is created from the results table. An example of such a list is given in Table 3, following the processing of scan numbers 300 to 432, corresponding to an elution time range of 5.0 minutes to 7.0 minutes, in the present example.

TABLE 3

List of peaks determined to be due to eluted compounds.

| Mass | Intensity | Centroid Elution Time | Peak Factor | Correlation Factor |
|---|---|---|---|---|
| 829.6774 | 8626 | 5.488 | 1000 | 0.7918 |
| 831.6815 | 3156 | 5.491 | 1000 | 0.8309 |
| 830.6814 | 5760 | 5.494 | 1000 | 0.9127 |
| 832.6827 | 1278 | 5.502 | 1000 | 0.9335 |
| 833.6764 | 415 | 5.502 | 1000 | 0.9092 |
| 834.6757 | 131 | 5.505 | 1000 | 0.9326 |
| 866.6518 | 1911 | 5.982 | 1000 | 0.8585 |
| 864.6480 | 17303 | 5.995 | 1000 | 0.9360 |
| 861.6530 | 79185 | 5.997 | 1000 | 0.9176 |
| 867.6508 | 528 | 5.998 | 1000 | 0.9328 |
| 868.6443 | 135 | 5.998 | 1000 | 0.9420 |
| 862.6554 | 54175 | 5.998 | 1000 | 0.9344 |
| 865.6489 | 6211 | 6.001 | 1000 | 0.9209 |
| 863.6478 | 35107 | 6.004 | 1000 | 0.9279 |
| 897.6230 | 836 | 6.077 | 1000 | 0.9366 |
| 893.6218 | 9026 | 6.078 | 1000 | 0.9038 |
| 895.6219 | 4517 | 6.081 | 1000 | 0.9323 |
| 896.6233 | 1939 | 6.082 | 1000 | 0.9461 |
| 894.6239 | 6333 | 6.086 | 1000 | 0.9559 |
| 898.6240 | 283 | 6.088 | 1000 | 0.9453 |
| 899.6228 | 82 | 6.091 | 1000 | 0.9558 |

Peaks identified to be candidates for being due to eluted compounds are then further processed to reveal clustering of peaks from the same compound. The peaks are converted to Gaussian peaks with a FWHH of 0.007 minutes and all peaks are added together. The resultant chromatogram reveals three peaks representing three compounds, as shown in FIG. 2. This data is then analysed for peaks and each detected peak represents a compound eluting at an elution time $RT_p$. The centroid elution times of all peaks within Table 3 are then compared to the elution times $RT_p$, and all peaks in Table 3 that have centroid elution times within +/−three times the uncertainty in the elution time measurements of $RT_p$ are considered to be components of the same compound. Comparison of FIGS. 2 and 7 illustrates the improved resolution of compounds eluted from the chromatography device afforded by the present invention.

Figure 9A:
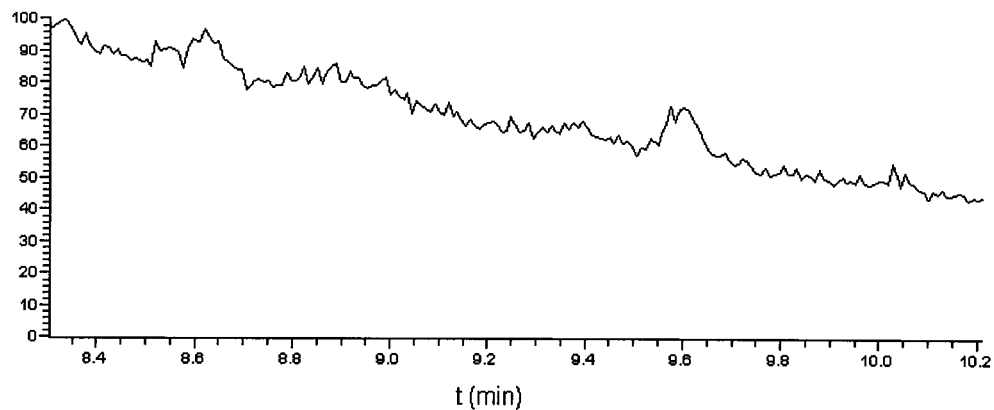
FIG. 9a shows a portion of a TIC from 8.30 to 10.21 minutes, such as would be produced from a LC, with relative abundance plotted against elution time.
Figure 9B:
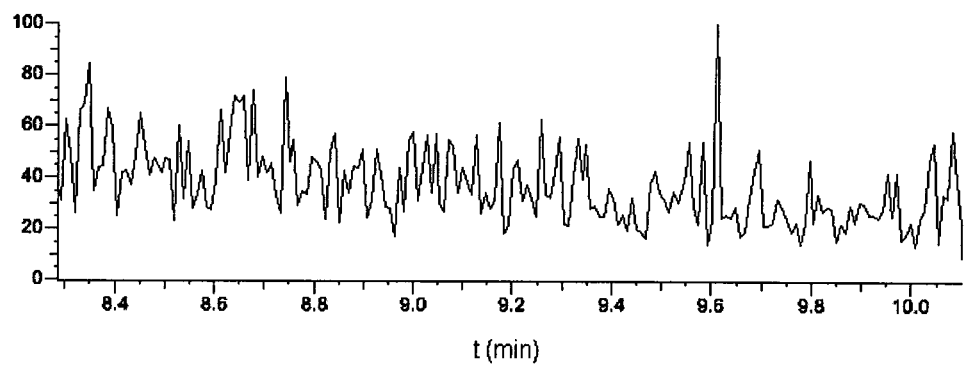
FIG. 9b shows the result of applying the method of Biller and Biemann to the TIC of FIG. 9a, in the form of a resolved TIC, with relative abundance plotted against elution time.
Figure 9C:
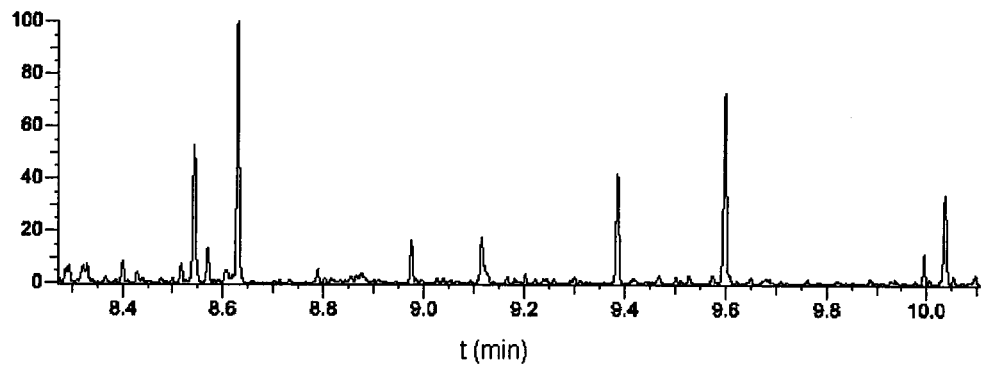
FIG. 9c shows the results of applying the present invention to the TIC of FIG. 9a in the form of a resolved TIC, with relative abundance plotted against elution time.

The present invention is compared with the prior art Biller and Biemann technique in FIG. 9. FIG. 9a shows a portion of a TIC from 8.30 to 10.21 minutes. The data in this figure differs from those in the previous examples described. FIG. 9b shows the result of applying the method of Biller and Biemann to the data of FIG. 9a, in the form of a resolved TIC. FIG. 9c shows the results from the present invention also in the form of a resolved TIC. Comparison of FIGS. 9b and 9c illustrates the two major advantages of the present invention, namely the high degree of background rejection and the increased time resolution over the prior art method, which together enable a far higher degree of resolution of compounds eluted from the chromatography device.

Useful improvements of the method include searching for co-eluting peaks in the full data set once an event has been detected, e.g. by a certain mass or retention time difference, or both, such as a search for isotopes, or for co-eluting quantitation masses, especially in labelling experiments (i-Traq, TMT, SILAC (stable isotope labeling with amino acids in cell culture), EPA 1613, etc.) as well as procedural improvements, including tracking of identified events in the combined time/spectral parameter space to avoid reprocessing of information which has already been allocated to a previously identified event.

Typical applications of the invention include analysis of proteins, peptides and metabolites of pharmaceuticals.

In the case of application to mass spectrometry, preferred ion sources are atmospheric pressure ion sources, including electrospray ionisation (ESI), and laser desorption ionisation, including MALDI. The method can be used for improved identification of compounds from plain spectra as well as from spectra of fragmented or reacted ions, or any combinations thereof. The processing of MS raw data with the algorithm is valuable in all cases where either the removal of unspecific mass traces or the clustering of coeluting components discriminate signals which are not the subject of interest. The reduced data set resultant from the method of the present invention allows further investigation in less time with a higher degree of confidence, without losing information. Any additional data processing step will work much faster on such condensed data sets. The improved RT resolution helps to separate components which have similar but not equal RTs.

All MS experiments with a high proportion of background ions will benefit from the discriminating capability of the algorithm. SILAC mass spectrometry quantitation particularly benefits from use of the invention. To determine the abundances of proteins between two (or more) samples, the growth medium of one sample is labeled with stable amino acid isotopes. To provide an automated software quantitation method for the calculation of the relative peptide abundances, both labeled and unlabeled (SILAC pairs) peptides must be identified. The SILAC quantitation methods take advantage of the background removal and clustering capabilities of the present invention, due to the fact that all isotope peptides of a SILAC pair are chemically identical and hence elute simultaneously, and the invention will group all isotopes of the SILAC pair within one cluster. Background removal and clustering simplifies and accelerates the further data processing steps of charge and isotope deconvolution and identification of SILAC pairs dramatically. Due to the improved RT resolution, peptides are better separated. This yields to less false positive pair identification and allows results with higher confidence. In a further improvement, the algorithm can specifically search for ions originally missing from a SILAC pair, once an ion has been identified. This improves the dynamic range of quantitation.

In metabolism applications, all isotopes of the same metabolite (small molecule) will coelute and so will be grouped together in one cluster. All further data processing steps can be performed on the events within one cluster e.g. charge state, isotope pattern deconvolution, identification of adducts, and neutral losses. This also yields better performing algorithms and results in a higher degree of confidence.

The method of the present invention is suitable for use with mass spectrometry data from ionisation sources without additional fragmentation, where—depending on the ionization method—only isotopes (ESI, API, MALDI) and charge states (ESI, Laserspray, APCI) are expected or where fragments are directly formed in the ionization process (EI; CI, as for example in the case of GC-MS, or "source CID" or "all ion fragmentation")

The method of the present invention is also suited for MS/MS data, especially for multiplexed data or in the case where simply all ions are subjected to fragmentation.

The method of the present invention can be applied to the case where there are two alternating modes of operation of the mass spectrometer: a mode with little or no fragmentation and a mode with substantial fragmentation. In such cases, the results from the two measurement modes can be correlated (i.e. the two measurement modes are subjected separately to the method of the invention) producing for example a precursor/product relation for events detected at the same position in the separation dimension, or, the two (or more) measurement modes are subjected to the method of the invention together, thus for example directly grouping precursor and product ions into the same eluted compound.

The method of the invention is well suited for advanced or post-processing. For example modifications of a substance by labels or metabolization could either be directly collected in step (f) by allowing fixed relations in the separation and spectroscopic dimensions, or—preferably—the produced events are screened for correlations such as mass differences from labels or mass and time differences from labels and or metabolites.

One major advantage of the invention is that it operates without heuristics or assumptions. All parameters can be determined from the data set at hand. This is one of the main benefits of the invention, as it makes sure that data are only grouped on the basis of their apparent properties, especially on the basis of whether their position in the separation dimension is the same within the precision of the separation method or not. This reduces the risk of skewing data by the application of inaccurate assumptions. In this spirit, even though a search for specific correlations in the separation and spectral dimension (e.g. the expectation of a pair of peaks with a certain mass difference to also have a certain difference in retention time) could be done as part of step (g) it is advantageously done in a separate later step.

One such later identification step could be to search for mass labels.

Mass labels could for example be iTRAQ or TMT reagents or the specific patterns from e.g. SILAC experiments. Notably, spectra containing multiply charged species could be deconvoluted for charge states between steps (a) and (c). Another such later identification step could be to search for likely metabolic relationships, e.g. a metabolic methylation, sulfuration or phosphorylation. The expected mass and retention time differences are usually well known from previous measurements or publications.

As used herein, including in the claims, unless the context indicates otherwise, singular forms of the terms herein are to be construed as including the plural form and vice versa.

Throughout the description and claims of this specification, the words "comprise", "including", "having" and "contain" and variations of the words, for example "comprising" and "comprises" etc, mean "including but not limited to", and are not intended to (and do not) exclude other components.

It will be appreciated that variations to the foregoing embodiments of the invention can be made while still falling within the scope of the invention. Each feature disclosed in this specification, unless stated otherwise, may be replaced by alternative features serving the same, equivalent or similar purpose. Thus, unless stated otherwise, each feature disclosed is one example only of a generic series of equivalent or similar features.

The use of any and all examples, or exemplary language ("for instance", "such as", "for example" and like language) provided herein, is intended merely to better illustrate the invention and does not indicate a limitation on the scope of the invention unless otherwise claimed. No language in the specification should be construed as indicating any non-claimed element as essential to the practice of the invention.

Any steps described in this specification may be performed in any order or simultaneously unless stated or the context requires otherwise.

All of the features disclosed in this specification may be combined in any combination, except combinations where at least some of such features and/or steps are mutually exclusive. In particular, the preferred features of the invention are applicable to all aspects of the invention and may be used in any combination. Likewise, features described in non-essential combinations may be used separately (not in combination).

The invention claimed is:

1. A method of improving the resolution of compounds eluted from a chromatography device comprising:
   (a) measuring spectroscopic data from an effluent eluted from a chromatography device as a function of elution time, the effluent containing eluted compounds;
   (b) identifying at least some peaks in intensity as a function of time in at least some of the measured spectroscopic data to form a first set of identified peaks;
   (c) discarding from the first set of identified peaks those peaks that are not due to an eluted compound thereby forming a second set of peaks from those retained;
   (d) transforming each peak in the second set of peaks into a first model peak centered on the elution time of each peak in the second set of peaks;
   (e) adding together some or all the model peaks created in step (d) to create a new chromatogram;
   (f) identifying at least some peaks in intensity in the new chromatogram;
   (g) grouping together all identified peaks in intensity in the second set of peaks having elution times within a given time period of identified peaks in intensity in the new chromatogram and assigning them to a single eluted compound thereby forming a processed data set;
   wherein steps (b)-(g) are performed by at least one of: (i) a computer running computer software or (ii) a dedicated electronic processor.

2. The method of claim 1 wherein in step (c) peaks are discarded on the basis of the intensity of the identified peak above a local background of the spectroscopic data.

3. The method of claim 1 wherein in step (c) peaks are discarded on the basis of a match between the shape of the identified peak and a second model peak shape.

4. The method of claim 1 wherein in step (c) peaks are discarded from the first set of identified peaks on the basis of measured peak intensity and measured peak width compared with expected peak intensity and expected peak width.

5. The method of claim 1 wherein in step (c) peaks are discarded on the basis of both the intensity of the identified peak above a local background of the spectroscopic data and on the basis of a match between the shape of the identified peak and a second model peak shape.

6. The method of claim 1 wherein the first model peak shape is based upon one or more of: a Gaussian peak shape, a bell-shaped peak shape, a Lorentzian peak shape, a parabolic peak shape or a triangular peak shape.

7. The method of claim 3 wherein the second model peak shape is based upon one or more of: a Gaussian peak shape, a bell-shaped peak shape, a Lorentzian peak shape, a parabolic peak shape or a triangular peak shape and has a full width at half height (FWHH) which is a linear function of the elution time at which the identified peak occurred.

8. A method according to claim 2 wherein a peak factor is determined for each identified peak of the measured spectroscopic quantities, the peak factor being representative of the intensity of the peak above the local background, and the peak factor (PF) is a function of:
   (i) the intensity of the identified peak, and
   (ii) at least one of: a noise on the measured spectroscopic quantity in the vicinity of the identified peak, and, the intensity of one or more minima in the vicinity of the identified peak.

9. A method according to claim 8 wherein the PF is defined by an expression containing the term $I_{maximum}/I_{minimum}$, where $I_{maximum}$ is intensity of the maximum of the identified peak and $I_{minimum}$ is the intensity of a minimum of the measured spectroscopic quantity local to the maximum of the identified peak in elution time.

10. A method according to claim 3 wherein correlation factors are determined between each of the identified peaks of the measured spectroscopic quantities and a second model peak shape, the correlation factor being representative of the match between the shape of the identified peak and the second model peak shape, the correlation factor (CF) being a function of the intensities of the identified peak and the second model peak shape at a plurality of points.

11. The method according to claim 10 wherein the correlation factor is a sample correlation coefficient.

12. A method according to claim 1 wherein in step (b) measured spectroscopic data is not analysed to identify peaks if the signal to noise ratio of the spectroscopic data as a function of time is less than a predetermined or calculated threshold.

13. A method according to claim 1 wherein the measured spectroscopic data have spikes removed in step (c).

14. A method according to claim 1 wherein the measured spectroscopic data are smoothed before step (d).

15. A method according to claim 1 wherein the given time period in step (g) is a function of the uncertainty of the measured spectroscopic data in the time domain.

16. A method according to claim 1 wherein the measured spectroscopic data are mass spectra.

17. A method according to claim 1 wherein the chromatography device comprises a liquid chromatograph.

18. A non-transitory computer readable medium encoded with a computer program containing instructions stored therein for causing a computer processor to perform a method of transforming measured spectroscopic data to improve resolution, the spectroscopic data representing an effluent eluted from a chromatography device as a function of elution time, the effluent containing eluted compounds, the method comprising steps of:

(a) identifying at least some peaks in intensity as a function of time in at least some of the measured spectroscopic data to form a first set of identified peaks;

(b) discarding from the first set of identified peaks those peaks that are not due to an eluted compound thereby forming a second set of peaks from those retained;

(c) transforming each peak in the second set of peaks into a first model peak centered on the elution time of each peak in the second set of peaks;

(d) adding together some or all the model peaks created in step (c) to create a new chromatogram;

(e) identifying at least some peaks in intensity in the new chromatogram;

(f) grouping together all identified peaks in intensity in the second set of peaks having elution times within a given time period of identified peaks in intensity in the new chromatogram and assigning them to a single eluted compound thereby forming a processed data set.

19. Apparatus for improving the resolution of compounds eluted from a chromatography device, comprising:

(a) a device for measuring spectroscopic data from an effluent eluted from a chromatography device as a function of elution time, the effluent containing eluted compounds;

(b) a module for identifying at least some peaks in intensity as a function of time in at least some of the measured spectroscopic data to form a first set of identified peaks;

(c) a module for discarding from the first set of identified peaks those peaks that are not due to an eluted compound thereby forming a second set of peaks from those retained;

(d) a module for transforming each peak in the second set of peaks into a first model peak centered on the elution time of each peak in the second set of peaks;

(e) a module for adding together some or all the model peaks created in step (d) to create a new chromatogram;

(f) a module for identifying at least some peaks in intensity in the new chromatogram; and (g) a module for grouping together all identified peaks in intensity in the new chromatogram having elution times within a given time period and assigning them to a single eluted compound thereby forming a processed data set.

* * * * *